(12) United States Patent
Cai et al.

(10) Patent No.: US 9,134,305 B2
(45) Date of Patent: Sep. 15, 2015

(54) MOLECULAR IMPRINTED NANOSENSORS

(75) Inventors: Dong Cai, West Newton, MA (US); Thomas C. Chiles, Norfolk, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 550 days.

(21) Appl. No.: 13/147,526

(22) PCT Filed: Feb. 3, 2010

(86) PCT No.: PCT/US2010/023068
§ 371 (c)(1),
(2), (4) Date: Jan. 6, 2012

(87) PCT Pub. No.: WO2010/144157
PCT Pub. Date: Dec. 16, 2010

(65) Prior Publication Data
US 2012/0118751 A1 May 17, 2012

Related U.S. Application Data

(60) Provisional application No. 61/149,859, filed on Feb. 4, 2009, provisional application No. 61/213,052, filed on May 1, 2009.

(51) Int. Cl.
*G01N 31/16* (2006.01)
*G01N 33/543* (2006.01)
*G01N 27/327* (2006.01)

(52) U.S. Cl.
CPC ...... *G01N 33/54346* (2013.01); *G01N 27/3278* (2013.01); *G01N 2600/00* (2013.01)

(58) Field of Classification Search
CPC ............ G01N 27/414; G01N 27/4146; G01N 27/327; G01N 27/3278
USPC ................ 422/82.01, 82.02, 83, 98, 551, 552
See application file for complete search history.

(56) References Cited

FOREIGN PATENT DOCUMENTS

WO WO-2008/133656 11/2008

OTHER PUBLICATIONS

C. Chen et al., "The electrochemical preparation of polyphenol with conductibility," Chinese Journal of Polymer Science (English Edition) vol. 20(4) pp. 309-316 (Jul. 2002).
C. Dong et al., "A molecular-imprint nanosensor for ultrasensitive detection of proteins," Nature Nanotechnology vol. 5(8), pp. 597-601 (Aug. 2010).
C.L. Choong, et al., "Carbon nanotube array: a new MIP platform," Biosensors and Bioelectronics, vol. 25(3), pp. 652-656 (Dec. 7, 2008).
International Preliminary Report on Patentability for PCT/US2010/023068 dated Aug. 9, 2011.
International Search Report for PCT/US2010/023068 mailed Nov. 30, 2010.

*Primary Examiner* — Jill Warden
*Assistant Examiner* — Dwayne K Handy
(74) *Attorney, Agent, or Firm* — Joseph M. Noto; Bond, Schoeneck & King PLLC

(57) ABSTRACT

An apparatus for detecting the presence of a target molecule is disclosed which includes a conductive nanostructure, a non-conductive polymer coating on at least a portion of the nanostructure, and a cavity formed in the polymer coating having a shape corresponding to the shape of the target molecule. A property of the nanostructure depends on the presence of the target molecule at the cavity.

27 Claims, 31 Drawing Sheets

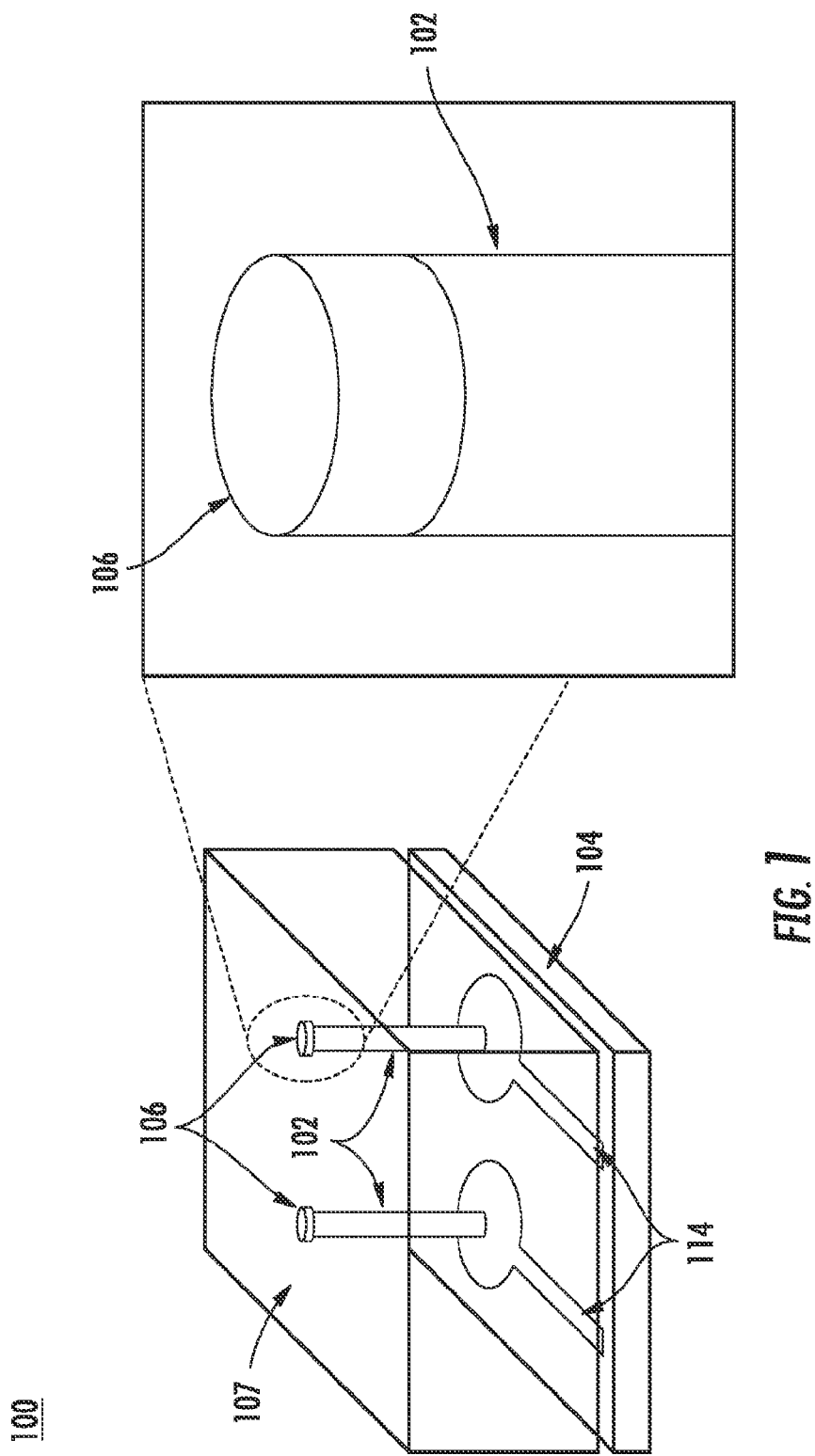

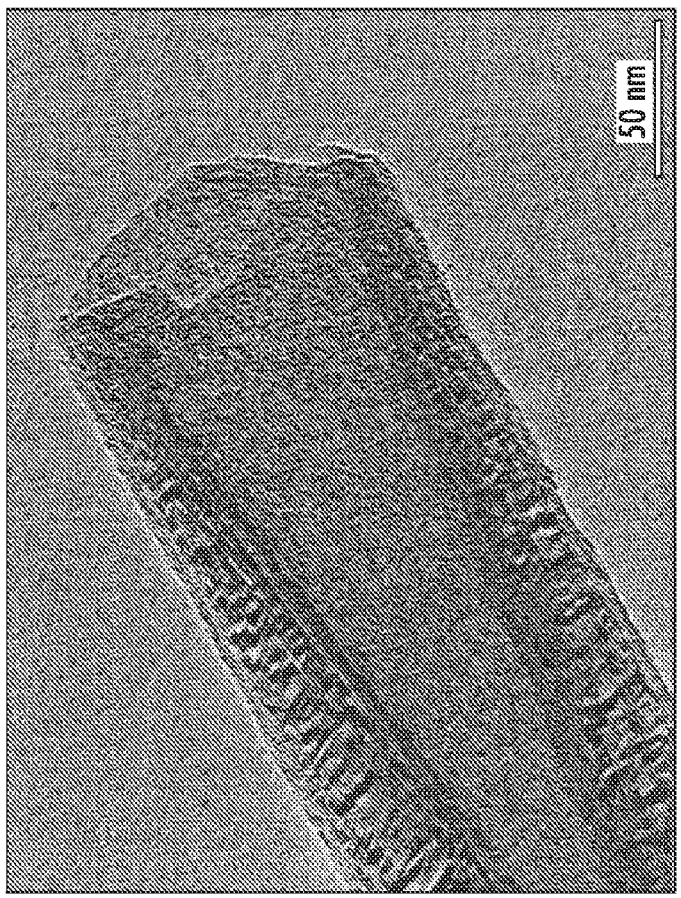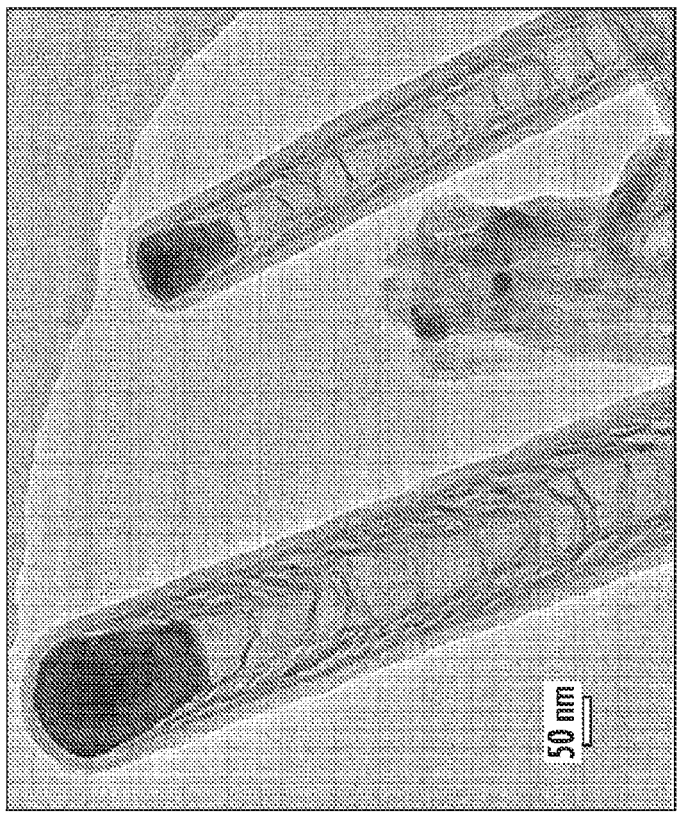
FIG. 5

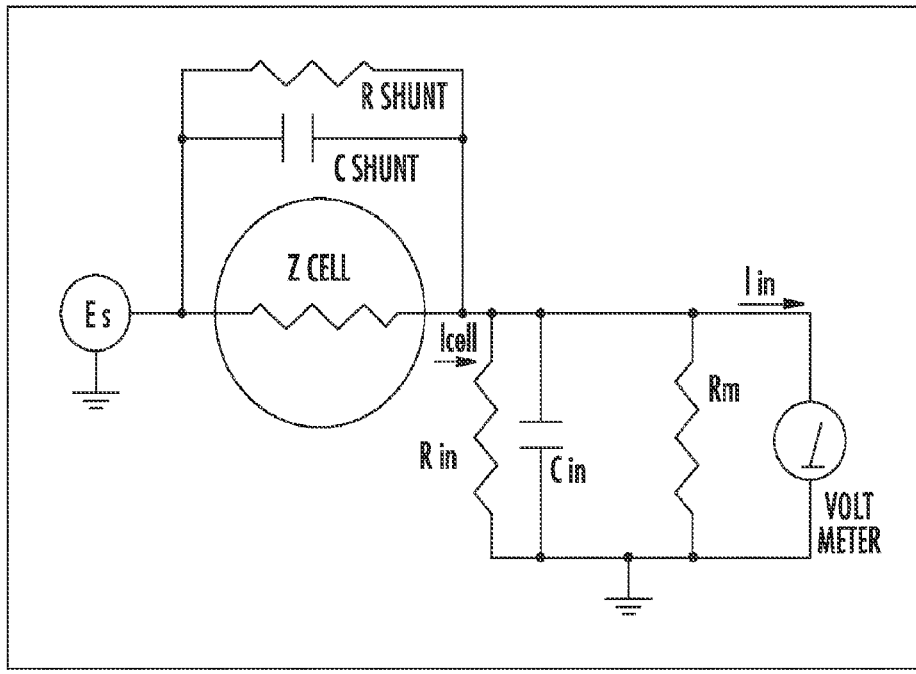

| | |
|---|---|
| $E_s$ | AN IDEAL SIGNAL SOURCE |
| $Z_{cell}$ | THE UNKNOWN CELL IMPEDANCE, i.e. COAX SENSOR IMPEDANCE |
| $I_{cell}$ | THE "REAL" CELL CURRENT |
| $R_m$ | THE CURRENT MEASUREMENT CIRCUIT'S CURRENT MEASUREMENT RESISTANCE |
| $R_{shunt}$ | AN UNWANTED RESISTANCE ACROSS THE CELL |
| $C_{shunt}$ | AN UNWANTED CAPACITANCE ACROSS THE CELL |
| $C_{in}$ | THE CURRENT MEASUREMENT CIRCUIT'S STRAY INPUT CAPACITANCE |
| $R_{in}$ | THE CURRENT MEASUREMENT CIRCUIT'S STRAY INPUT RESISTANCE |
| $I_{in}$ | THE MEASUREMENT CIRCUIT'S INPUT CURRENT |

$$Z_{cell} = E_s * R_m / V_m$$

FIG. 11

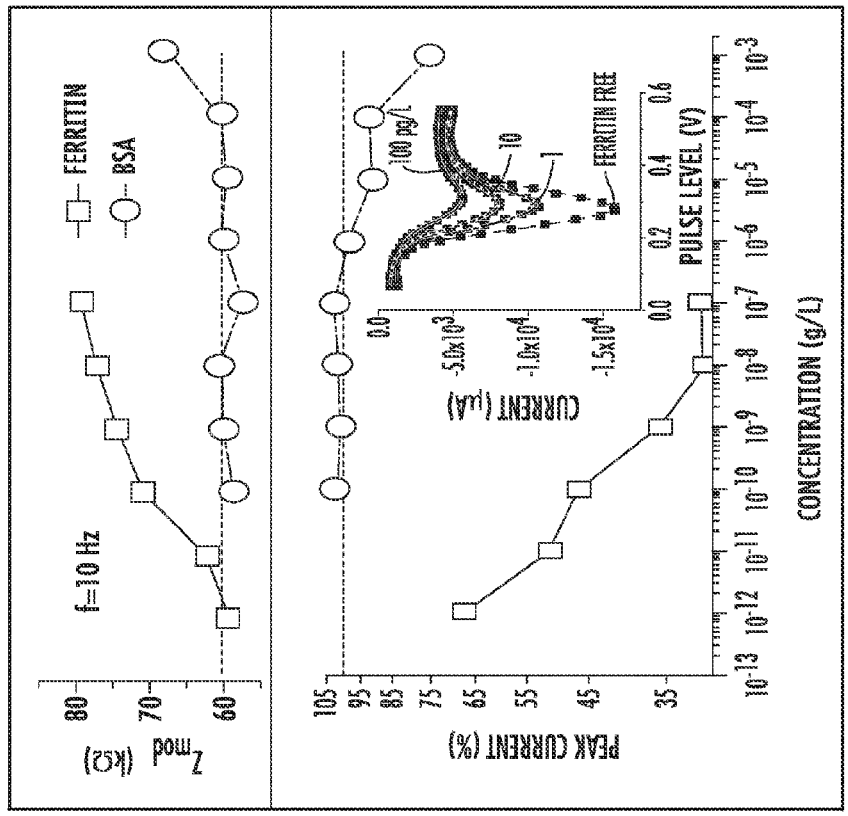
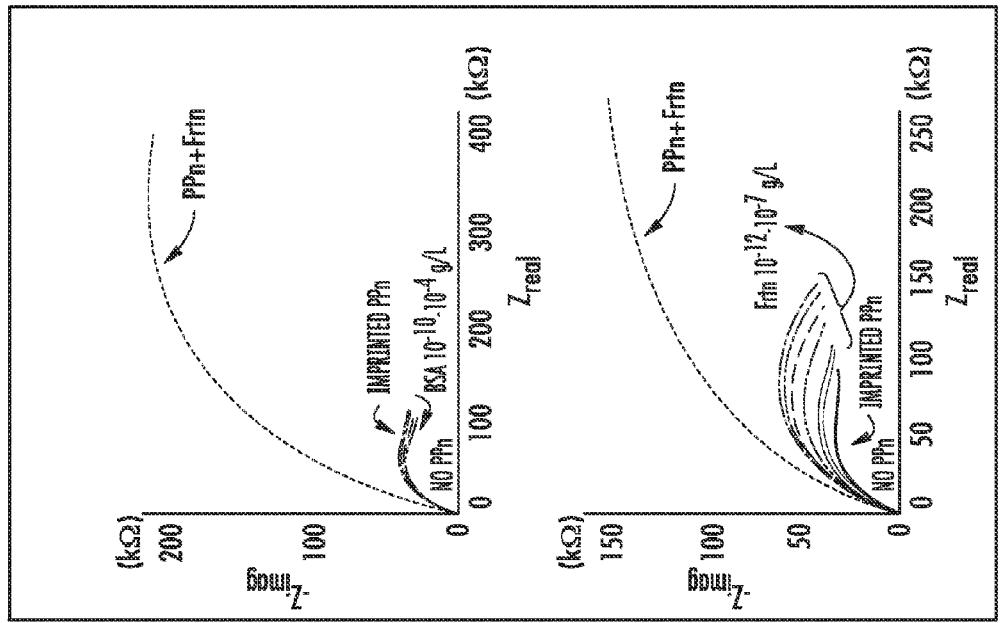
FIG. 13B
FIG. 13A

MOLECULAR IMPRINTED NANOSENSORS

RELATED APPLICATIONS

This application is the U.S. National Stage of PCT International Application Number PCT/US2010/023068, filed Feb. 3, 2010, which claims benefit of U.S. Provisional Application Ser. No. 61/149,859 filed Feb. 4, 2009 and U.S. Provisional Application Ser. No. 61/213,052 filed May 1, 2009, the entire contents of each of which are incorporated herein by reference.

STATEMENT OF GOVERNMENTAL INTEREST

This invention was made with Government Support under Contract Number PHY-0804718 awarded by the National Science Foundation and Contract Numbers FA8601-07-P-0548 and W911QY-08-P-0782 awarded by the Department of the Navy. The Government has certain rights in the invention.

BACKGROUND

This disclosure is related to sensors and, more particularly, sensors featuring molecularly imprinted polymers.

Sensors capable of detecting specific chemical agents such as proteins have application in a number of areas including chemical or pharmaceutical process monitoring, environmental surveillance, early stage cancer detection, anti-biowarfare detections, explosive detection, real time biological detections in vivo or in vitro, etc. In typical applications, it is desirable that the sensor be able to identify the presence of a specific target molecule in real time and with high sensitivity.

Molecular imprinting is a technique to create template-shaped cavities in a material, e.g. a polymer. The cavities act as a "memory" of the template molecules, and so may be used in molecular recognition. Molecularly imprinted materials are typically prepared using a template molecule and functional monomers that assemble around the template and subsequently get cross linked to each other. The functional monomers, which are self-assembled around the template molecule by interaction between functional groups on both the template and monomers, are polymerized to form an imprinted matrix (commonly known as a molecularly imprinted polymer or "MIP"). Then the template molecule is removed from the matrix under certain conditions, leaving behind a cavity complementary in size and shape to the template. The obtained cavity can work as a selective binding site for a specific target molecule.

SUMMARY

This disclosure is directed to devices, and techniques including the combination of a nanosensor with molecular imprinting technology. In some embodiments, a non conductive nanocoating (e.g. a polyphenol nanocoating) is established on a nanostructure, e.g. a conductive carbon nanotube (CNT) array. Proteins (or other target molecules) can be incorporated with the polymer layer and then washed out to create protein imprinted cavities in the polymers. The imprints hold an intrinsic affinity to the imprinting proteins that enables specific recognition. The protein-polymer interaction can be measured as an impedance change, although other detection methods may be used. Using the imprinting method, one may be able to detect a protein (or other target molecule) of interest without the use of antibodies or epitopes of antibodies.

The devices and techniques described herein may be used, for example, in early stage cancer detection, pharmaceutical process monitoring, environmental surveillance, anti-biowarfare detections, and real time biological detections in vivo or in vitro.

In one aspect, an apparatus for detecting the presence of a target molecule is disclosed which includes a conductive nanostructure, a non-conductive polymer coating on at least a portion of the nanostructure, and a cavity formed in the polymer coating having a shape corresponding to the shape of the target molecule. A property of the nanostructure depends on the presence of the target molecule at the cavity.

Some embodiments include a detection unit configured to produce a signal indicative of the presence of the target molecule at the cavity based on a measured change in the property of the nanostructure.

In some embodiments, the thickness of at least a portion of the non-conductive polymer coating is less than or about equal to than the size of the cavity. In some embodiments the thickness of the non-conductive polymer coating is less than about 25 nm, less than about 15 nm, less than about 10 nm, or smaller.

In some embodiments, the polymer coating is self limiting under electro polymerization. In some embodiments, the coating includes a polyphenol film.

In some embodiments, the nanostructure includes a carbon nanotube. In some embodiments, the nanostructure includes an array of substantially aligned carbon nanotubes each extending from a surface to a respective distal tip. Some such embodiments further include a protective layer surrounding the array such that only the distal tip of each nanotube extends from the layer. The non-conductive polymer coating includes a film on the distal tip of each nanotube.

In some embodiments, the property of the nanostructure includes the impedance of the nanostructure. In some embodiments, the impedance of the nanostructure depends on the presence of the target molecule at the cavity.

Some embodiments include a plurality of cavities formed in the polymer coating each having a shape corresponding to the shape of the target molecule. The impedance of the nanostructure depends on the occupation of the cavities by target molecules.

In some embodiments, the detection unit is configured to produce a signal indicative of the concentration of target molecules present in an environment proximal to the nanostructure, the signal being based on the impedance of the nanostructure. In some embodiments, the detection unit is configured to produce a signal indicative of the concentration of target molecules with a sensitivity of about 10 picograms per liter or less. In some embodiments, the detection unit is configured to produce a signal indicative of the concentration of target molecules with a sensitivity of about 1 picogram per liter or less. In some embodiments the target molecule includes ferritin.

In some embodiments, the nanostructure includes at least one from the list consisting of: a nanoparticle, a nanorod, a nanowire, a nanotube.

In some embodiments, the property includes at least one selected from the list of: a mechanical property, a chemical property, and electrochemical property, an optical property, and an electrical property.

In some embodiments, the target molecule includes at least one selected from the list including: a protein molecule, a pheromone molecule, an explosive molecule.

In another aspect a method is disclosed including the steps of forming a conductive nanostructure, forming a non-conductive polymer coating on the nanostructure in the presence of a template molecule to entrap a template molecule in the polymer coating, and removing the entrapped template molecule to form a cavity in the polymer coating having a shape corresponding to the shape of the target molecule. A property of the nanostructure depends on the presence at the cavity of a target molecule having a shape corresponding to the template molecule.

In some embodiments, the thickness of at least a portion of the non-conductive polymer coating is less than or about equal to than the size of the cavity.

In some embodiments, the thickness of the non-conductive polymer coating is less than about 25 nm, less than about 15 nm, less than about 10 nm, or smaller.

In some embodiments, forming the non conductive polymer coating on the nanostructure includes: forming a film of non-conductive polymer on a portion of the nanotube by electropolymerization. The final thickness of the film is self limited by the production of a voltage drop across the thickness of the film as it forms on the nanotube.

In some embodiments, forming the nanostructure includes forming a carbon nanotube. In some embodiments, forming the nanostructure includes forming an array of substantially aligned carbon nanotubes each extending from a surface to a respective distal tip. Some embodiments include forming a protective layer surrounding the array such that only the distal tip of each nanotube extends from the layer. The non-conductive polymer coating includes a film the distal tip of each nanotube. Forming the non conductive polymer coating on the nanostructure includes forming a non-conductive polymer film on each distal tip.

In some embodiments, removing the entrapped template molecule to form a cavity in the polymer coating having a shape corresponding to the shape of the target molecule includes applying a developing fluid to the polymer coating.

In some embodiments, the developing fluid includes de-ionized water; phosphate buffered saline; phosphate buffered saline including acetic acid or sodium dodecyl sulfate Some embodiments include monitoring the property of the nanostructure to determine information indicative of the presence of target molecule at the cavity.

Some embodiments include determining information indicative of a concentration of target molecules present in an environment proximal to the nanostructure based on the impedance of the nanostructure.

In some embodiments, the determining information indicative of a concentration of target molecules includes determining information with a sensitivity of about 10 picograms per liter or less, or 1 picograms per liter or less. In some embodiments, the target molecule includes ferritin.

In some embodiments, the nanostructure includes a nanoparticle, a nanorod, a nanowire, or a nanotube.

In some embodiments, the property includes a mechanical property, a chemical property, an electrochemical property, an optical property, or an electrical property.

In another aspect, a method of selectively detecting a chemical substance is disclosed including: providing one or more sensors. Each sensor includes: a conductive nanostructure; a non-conductive polymer coating on at least a portion of the nanostructure; and a cavity formed in the polymer coating having a shape corresponding to the shape of the target molecule (where a property of the nanostructure depends on a presence of the target molecule at the cavity); and a detection unit configured to produce a signal indicative of the presence of the target molecule at the cavity based on a change in the property of the nanostructure. The method further includes using the one or more sensors, generating a signal indicative of the property of the nanostructure which depends on the presence of the target molecule at the cavity, and processing the signal to determine information indicative of presence of the target molecule at the cavity.

In some embodiments, for each of the one or more sensors, the thickness of at least a portion of the non-conductive polymer coating is less than or about equal to than the size of the cavity.

Some embodiments include determining information indicative of a concentration of target molecules present in an environment proximal to the nanostructure based on the impedance of the nanostructure. Some embodiments include determining the information indicative of the concentration of target molecules at a sensitivity of about 10 picograms per liter or less, or 1 picogram per liter or less.

In another aspect, a system for detecting a target molecule is disclosed which includes a sensor array. The sensor array includes one or more sensors, each sensor including: a conductive nanostructure, a non-conductive polymer coating on at least a portion of the nanostructure, a cavity formed in the polymer coating having a shape corresponding to the shape of the target molecule, and a detection unit configured to produce a signal indicative of the presence of the target molecule at the cavity based on a change in the property of the nanostructure. A property of the nanostructure depends on a presence of the target molecule at the cavity. The system also includes a liquid coating on the sensor array and includes a gas-liquid interface; and a binding agent which binds with the target molecule near the air liquid interface, and directs the bound molecules through the liquid to the sensor array.

Some embodiments include a gas permeable membrane located at the gas-liquid interface. The membrane is permeable by the target molecule.

In some embodiments, the binding agent releases the bound target when it comes in proximity to the sensor array.

As used herein, the phrase "size of the cavity" is to be understood as the length of the diameter of the smallest sphere which can encompass the entire cavity.

A nanostructure may include an object having a characteristic size along at least one dimensions which is on the order of tens of nanometers or less. For example nanotubes, nanorods, or nanowires have at least two dimensions on the nanoscale. A nanoparticle (e.g. a nanosphere) has three dimensions on the nanoscale.

Various embodiments may include any of the features described herein, either alone or in any combination.

Unless otherwise defined, all technical and scientific terms used herein have the same meaning as commonly understood by one of ordinary skill in the art to which this invention belongs. In the event that the definition of a technical and scientific term found in material incorporated by reference conflicts with a definition found in this application, the definition found in this application holds.

BRIEF DESCRIPTION OF THE DRAWINGS

FIG. 1 illustrates a molecular imprint nanosensor.

FIG. 1A illustrates a molecular imprint nanosensor.

FIG. 5 shows electropolymerized carbon nanotubes.

FIG. 11 shows an EIS measurement system for use with a molecular imprint nanosensor.

FIGS. 13 and 14 illustrates the detection sensitivity and selectivity of an exemplary molecular imprint nanosensor.

DETAILED DESCRIPTION

MIP Sensor

Figure 7A:
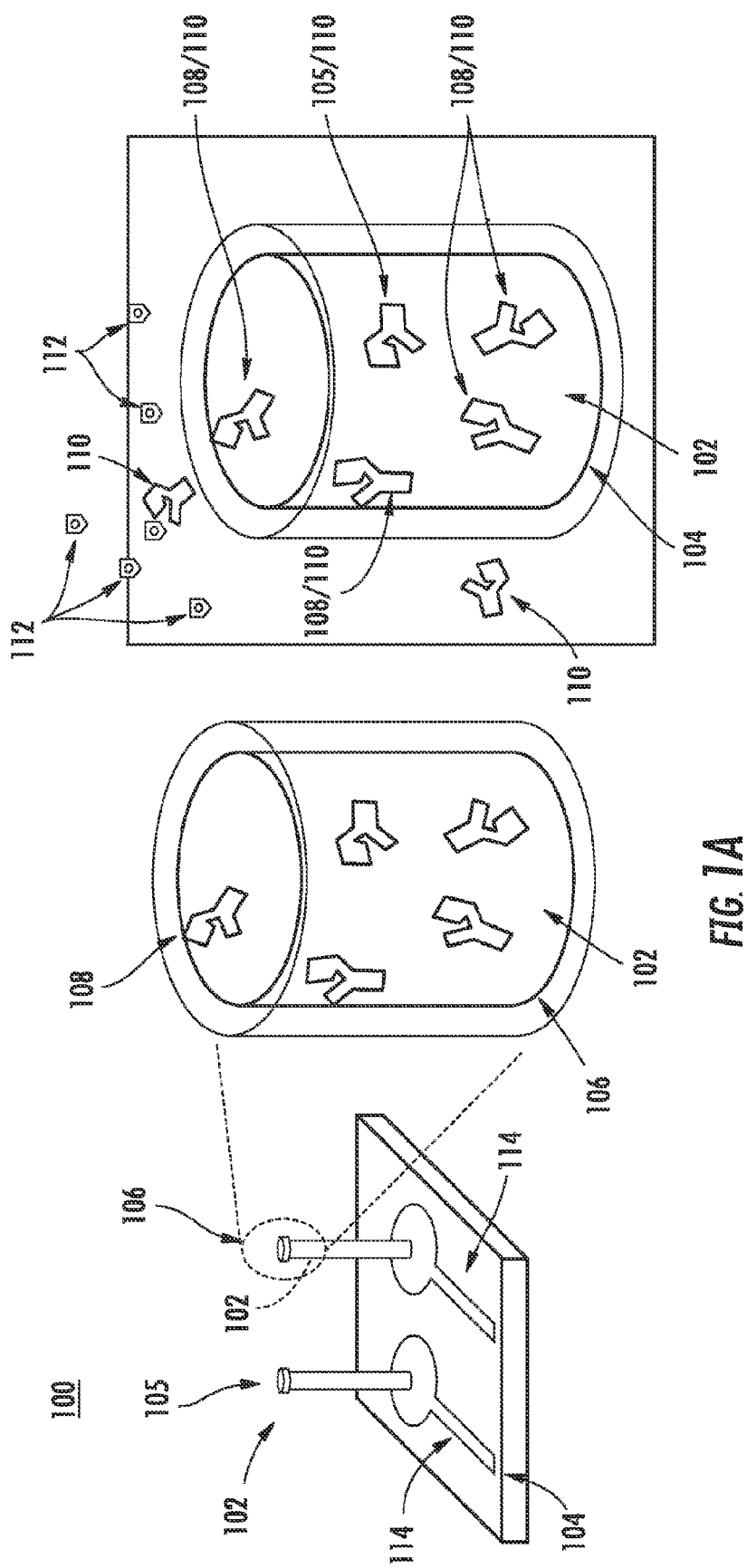
FIG. 7 illustrates the trapping of a ferritin template molecule.

Referring to FIG. 1, in one embodiment a sensor device 100 includes one or more nano-structures 102. As shown, the nanostructures 102 are two conductive carbon nano-tubes (CNTs) grown vertically on a substrate 104. A portion of the nanostructure 102 is coated with a non-conductive molecularly imprinted polymer (MIP) 106. As shown in the inset of FIG. 1, only the tips of the CNTs are coated with the MIP film 106. The CNTs may be embedded in a protective material 107 (e.g. a spin coated UV cured photoresist). However, in various embodiments other portions or the entirety of the CNTs may be coated, e.g. as shown in FIG. 1A. The tips of the CNTs may be exposed or otherwise extend out from a protective material 107 (e.g. a spin coated UV cured photoresist).

As described in detail below, the MIP 106 is formed to include template cavities 108 having shapes corresponding to a target molecule 110, as shown in FIG. 1A (center). When the sensor device 100 is placed in the vicinity of target molecules 110, the target molecules 110 can bind to the cavities 108 as shown in FIG. 1A (right). Other molecules 112, having shapes which do not correspond to that of the template cavities 108 will not bind to the cavities 108 (or will do so much less easily than the target molecule). The presence of the target molecules 110 bound to the MIP 106 act to change one or more physical properties of the sensor. In the embodiment shown, the presence of target molecules 110 in the insulating MIP film 104 act to reduce the resistivity of the film. In some embodiments, the change in the physical property may correspond to the number of cavities 108 occupied.

As described in detail below, one or more electrodes 114 couple the CNTs to a detector unit which measures changes in one or more physical properties of the CNT 102 and/or the film 106, e.g. impedance changes, which indicate the presence of the target molecule 110.

Typically, the magnitude of change of the physical will be related to the concentration of target molecules 110 in the environment near the CNTs. The sensitivity of the detector 100 may be defined by the lowest such concentration that can be accurately and reliably detected.

In some embodiments, the thickness of the MIP film 106 is on the order of the size of the target molecule. For example, a ferritin protein molecule has a diameter of about 3 nm. A sensor 100 of the type shown in FIGS. 1 and 1A may employ an MIP film 106 having a thickness of about 10 nm. Due to the comparable size of the target molecule 110 and the MIP film thickness, the presence of target molecules 110 at the cavities 108 in the MIP film 104 may lead to relatively large changes in the resistivity of the film. These large changes provide a high level of detection sensitivity.

Fabrication

Figure 2:
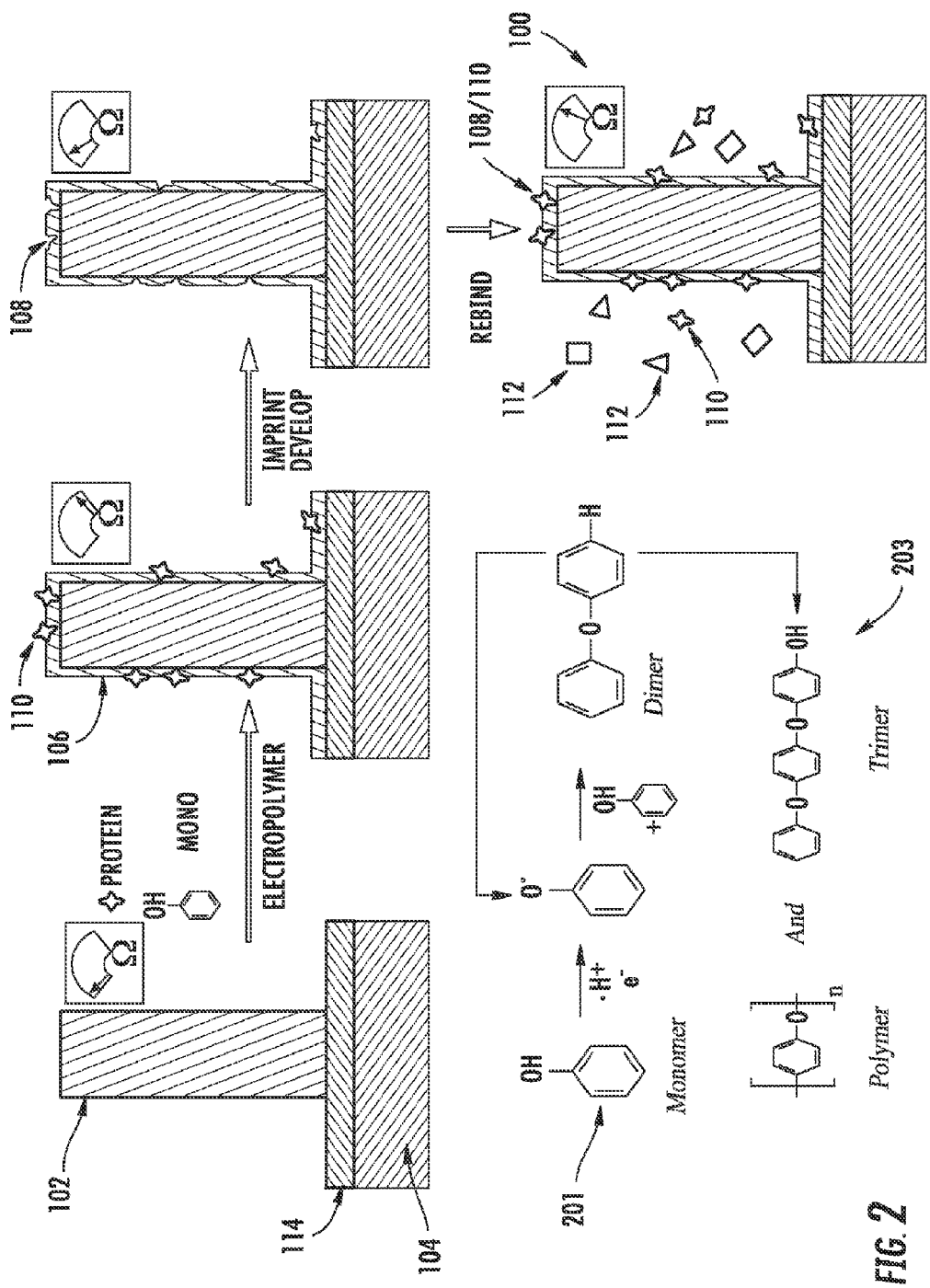
FIG. 2 illustrates the fabrication of a molecular imprint nanosensor.

FIG. 2 illustrates the fabrication of an imprinted nanosensor 100 of the type described above. Vertically aligned carbon nanotubes (CNTs) 102 provide the basic structure and surface of the sensor 100. Any suitable technique can be used to form the CNTs. For example, in some embodiments, a plasma enhanced chemical vapor deposition (PECVD) process may be used for growing of an aligned CNT array.

Several types of CNT array structures may be used. For example, in some embodiments, a high density CNT array (hCNTA) may be formed. In one such embodiment, an area (e.g. 25×25 mm) of a silicon wafer is coated with chromium and nickel layers of having a thickness of e.g., 350 and 30 nm, respectively. A base pressure of $10^{-6}$ Torr may be used before the introduction of acetylene and ammonia gases. The growth pressure may be e.g. $10^{-20}$ Torr, and the growth time may be e.g. 1-10 min according to the desired nanotube length. The substrate temperature may be maintained below e.g. 660° C. during the deposition process.

In some embodiments, a periodic and low density CNT array (lCNTA) may be prepared. For example, in one such embodiment Ni is deposited on chromium coated Si wafer through a polystyrene microsphere monolayer by electron beam evaporation. Periodically patterned Ni is revealed after removal of the spheres by sonication. Then the Ni is annealed and plasma etched at 550° C. for 2 min.

In some embodiments, a CNT tip array (tCNTA) of the type shown in FIG. 1 may be used. A tCNTA may be formed by embedding an lCNTA in a protective material (e.g. a photoresist) which is mechanically polished to reveal the CNT tips only. For example, in one such embodiment, SU8-2002 photoresist is spun on an lCNTA (e.g. at 3000 rpm for 30 s). Following a soft bake e.g. for 5 min on a hot plate set at 100° C., the SU8 is cross-linked by exposure to UV light for 3 min. Then the sample is then hard baked, e.g. at 150° C., overnight. The resulting chip may then be polished e.g. until the desired tip pattern emerges from the SU8 coating as observed with an SEM.

Figure 4:
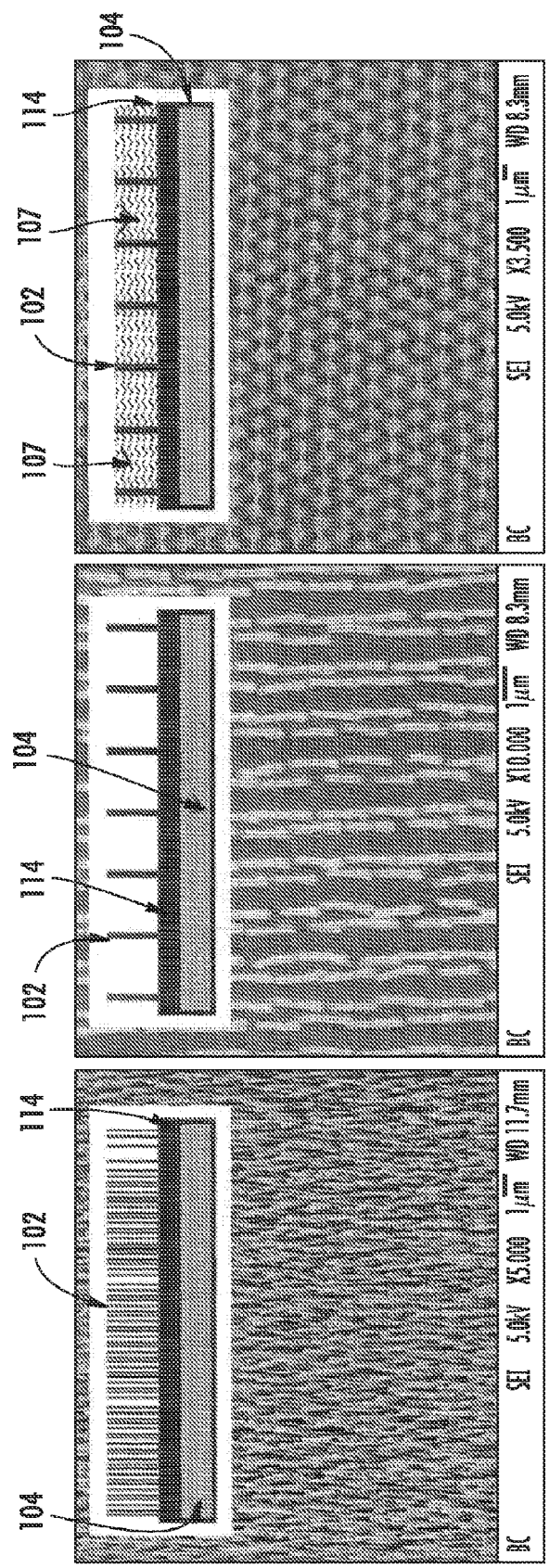
FIG. 4 shows three types of exemplary carbon nanotube arrays.

FIG. 4 shows scanning electron microscopy (SEM) images of hCNTA (left), lCNTA (center) and tCNTA (right). The embedded sketches show the cross-section of the arrays.

Referring back to FIG. 2, a non-conductive polymer 106, e.g. polyphenol, is electropolymerized on the electrically active surface of the CNT 102 in the presence of a target molecule 110 (as shown, a protein). A voltage applied to the CNT 102 causes the oxidation of monomers 201 present in solution surrounding the CNTs. This oxidation drives a polymerization process 203 to form the film 106. For example, the inset of FIG. 2 illustrates the electropolymerization process for a polyphenol (PPn) film.

In embodiments where the polymer film is non-conducting, the electropolymerization process 203 may be self limiting. Accumulated thickness of the non-conducting film 106 on the CNT surface results in a voltage drop across the film. The major reaction will stop when the voltage at the solution side of the film is too low to oxidize more monomers 201 (e.g. phenols).

The self-limiting deposition process allows for the reproducible and, in some embodiments, substantially pinhole free thin film coating with nanoscale thickness on the order of the size of the target molecule (e.g. 10 nm or less).

The entrapped target proteins 110 can be removed by a developing buffer leaving cavities 108 (sometimes referred to as "vials") in the film. The topological and conformational information of the target protein molecule 110 will be imaged and kept by the surface of the cavities 108, which are the imprints of the target protein molecule 110. The imprint holds the capability of recognition that only specifically allows the target protein molecule 110 with the exact match of the surface feature of the cavity 108 to rebind.

Due to the non-conductive nature of the nanofilm coating 106, significant impedance (indicated in the figure as $\Omega$) changes will be observed at the stage of target protein molecule entrapment, imprint development and target rebinding. For molecular sensing, the signal due to the rebinding can be detected by impedance measurement and/or other electrochemical methods. High sensitivity will be facilitated by the extremely thin film 106 with a thickness that is comparable to the size of target molecules 110. For example, proteins such as ferritin have a characteristic size on the order of a few tens of nanometers. As noted about, self-limiting non-conductive polymer films with thickness of 10 nm or less may be produced using electropolymerization.

In some embodiments, the sharp features of the coated nanostructures 102 (e.g. CNTs) may enhance the self limiting nanofilm MIP coating 106. Although not wishing to be limited by theory, in some embodiments this enhancement may result from sharp electric field gradients associated with sharp spatial features (e.g. extreme surface curvatures) of the CNTs. Due to the extreme curvature of CNT surface, the electric field in the vicinity of CNTs will be intensified and may be helpful to produce more condensed polymer structures with higher resistivity. Moreover, the CNT can also generate a decaying field profile, under which the deposition could stop at a short distance from the CNT surface because of the drop of electrical potential.

Figure 2B:
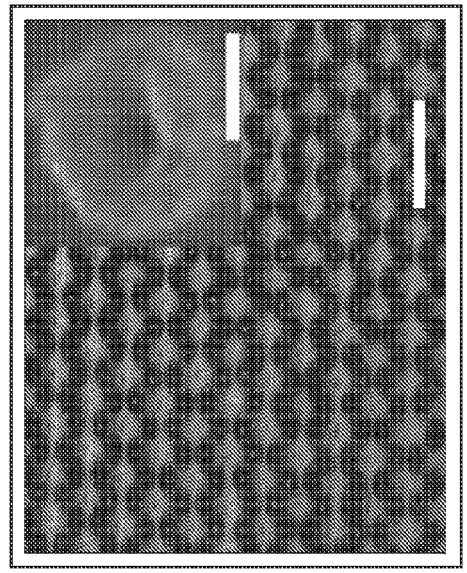
FIG. 2B is an SEM image of a carbon nanotube tip array (tCNTA)
Figure 2C:
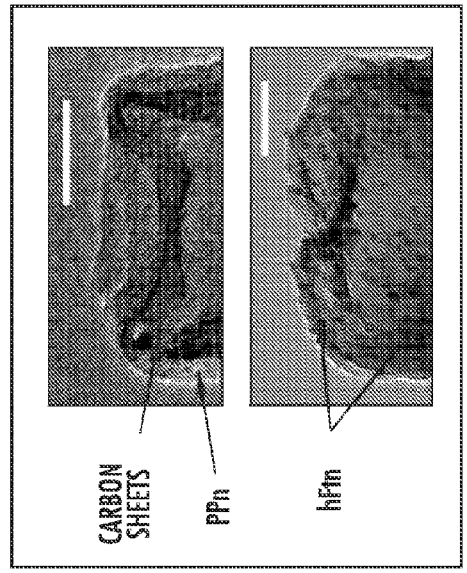
FIG. 2C shows SEM images of a molecular imprint polymer on the tip of a carbon nanotube.
Figure 2A:
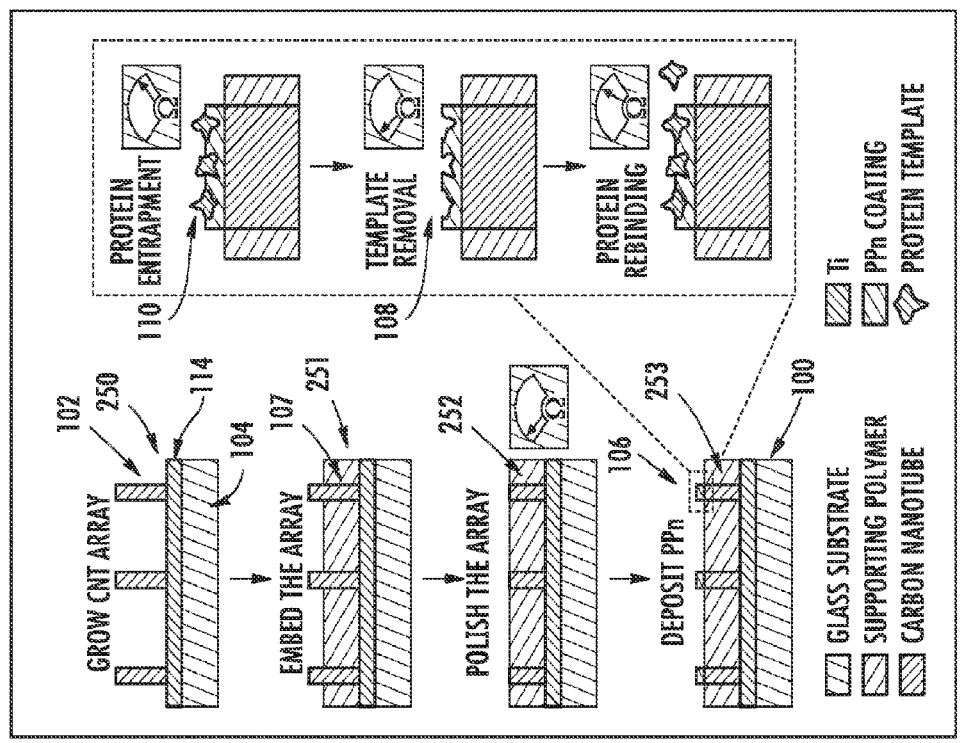
FIG. 2A illustrates the fabrication of a molecular imprint nanosensor.

FIG. 2A illustrates a process for fabricating an embodiment of a sensor 100 featuring a tCNTA structure. In a first step 250, an array of CNTs 102 are formed over electrode 114 on substrate 104. In a second step 251, the array is embedded in a protective material 107. For example, in one embodiment CNT array is embedded in SU8-2002 photoresist spun on the array at 3000 rpm for 30 seconds. Following a soft bake for 5 min at 100° C., the SU8 is cross-linked by exposure to UV light for 3 min and then the sample was incubated at 150° C. overnight.

In a third step 252, the embedded array is polished (e.g. using chemical mechanical polishing, vibratory polishing, or any other suitable technique) to expose the tips of CNTs 102. For example, in one embodiments, the embedded array is polished with a vibratory polisher e.g. of the type available from Buehler (41 Waukegan Road Lake Bluff, Ill. 60044 USA) with 80% power level for 6-9 hrs until the pattern emerged from the SU8 coating with confirmation by SEM.

In a fourth step 253, an MIP film 106 is forms on the tips of CNTs. As described above, film 107 may be formed using an self limiting electropolymerization process. As shown in the inset, the film 106 may be formed in the presence of target molecules 110, some of which are trapped in the film. The target molecules 110 may be removed using a developing process, leaving corresponding cavities 108. For example, in one embodiment, the entrapped target molecule 100 may be a protein (as shown ferritin) entrapped in a non conducting polymer coating 106 (as shown PPn). For imprint development, the ferritin-entrapping PPn coating is rinsed and incubated (e.g. overnight) in deionized water at room temperature. Alternatively, a developing buffer containing 5% acetic acid and 10% sodium dodecyl sulfate (SDS) may be used for higher protein extract efficiency.

FIG. 2B shows an SEM image of a polished CNT array after PPn coating as in fourth step 253 (inset: the CNT cross-section showing the centered pit after polishing, scale bars are 2 μm and 100 nm, respectively). FIG. 2C shows a TEM images of the CNT tips where the top image is the tip of PPn, scale bar 50 nm, and the bottom image shows the PPn plus entrapped hFtn coated CNT tips (scale bar 70 nm). As shown in FIGS. 2B and 2C, in one embodiment, the CNT tips exhibit open cross-sections with centered cavities. Transmission electron microscopy (TEM) shows that the PPn was uniformly deposited on the CNT tips, forming a pinhole-free 13 nm thick film. Co-deposition of human ferritin (hFtn) is visualized in the TEM image due to the contrast enhancement by the crystalline cores of the ferritin proteins (FIG. 2C). The diameters of the observed iron cores are between 5 to 8 nm. The comparable values of the PPn thickness and the diameter of protein particle result in the huge impedance change, allowing for high detector sensitivity.

Figure 3:
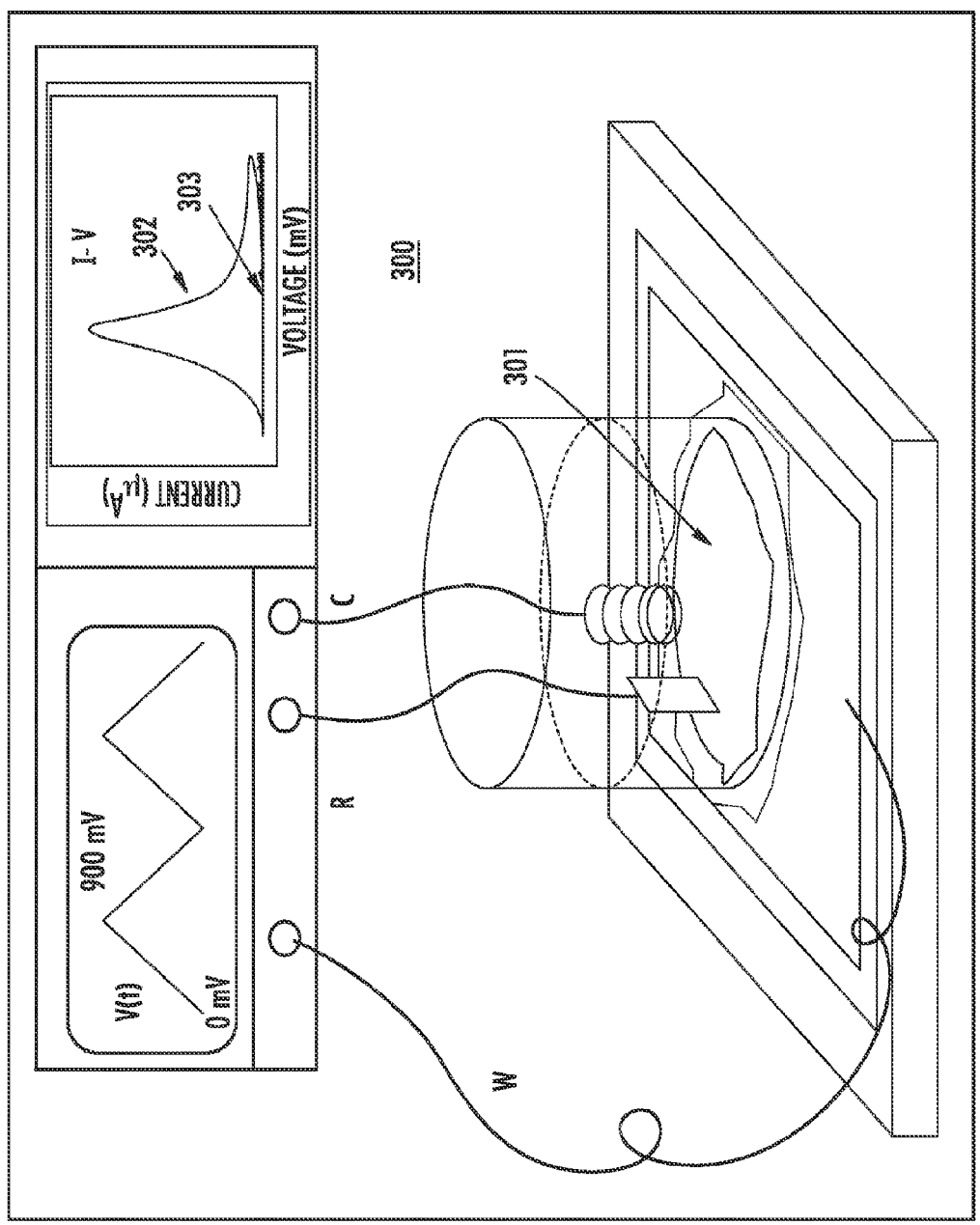
FIG. 3 illustrates an electrochemical device for use with a molecular imprint nanosensor.

FIG. 3 illustrates an exemplary electropolymerization system 300 for coating an array of CNTs with a PPn film. In a three-electrode electrochemical system, an array of nanostructures (as shown CNT array 301) is connected as working electrode (W), while Ag/AgCl and Pt wires serve as reference (R) and counter (C) electrodes respectively. Cyclic voltammetry (CV) is conducted by scanning voltage (e.g. from 0 to 900 mV as shown in the left inset) between the W and C electrodes. Phenol is dissolved e.g. together with $Na_2CO_3$ in water. The pH may be held stable. The reaction buffer for a typical embodiment may be 5 mM phenol supplemented phosphate buffered saline (PBS) at pH=7.4. The CV may be performed over multiple cycles, e.g. five times. Of course, these electropolymerization parameters may be adjusted based the application at hand.

In some embodiments where a PPn film is produced, phenol is oxidized at 200 to 400 mV and produces a large peak current (illustrated in the I-V plot of the right inset) in the first scan 302. Due to the formation of a non-conducting polyphenol coating on the CNT electrode, the following scans 303 typically have a reduced or even no oxidation current peak. In some embodiments, the current level may be reduced to about hundred times lower (or even less) than the first oxidation peak. The CNT array may maintain its original morphology with little collapse due to the surface tension during the sample drying after deposition. This process may be used to form a compact and uniform PPn coating on CNTs.

FIG. 5 (left) shows a PPn coating by transmission electron microscopy (TEM) on both hCNTA and lCNTA. FIG. 5 (right), is a TEM image show internal surface coating by PPn of a top-opened CNTs that is an analogue of the tCNTA. The internal and external PPn exhibit the similar thickness.

As shown in FIG. 5, the self limiting electropolymerized PPn on a CNT may form an ultra thin nanocoating e.g., with a thickness in the range of around 10-17 nm. In the example shown, the film is very uniform, compact and substantially pinhole free. The CNT array retains its morphology after the deposition. Further reduction of the PPn thickness, e.g. to 7 nm, may be obtained by introducing a dopant (e.g. sulfur) that helps to increase PPn resistivity.

Figure 6C:
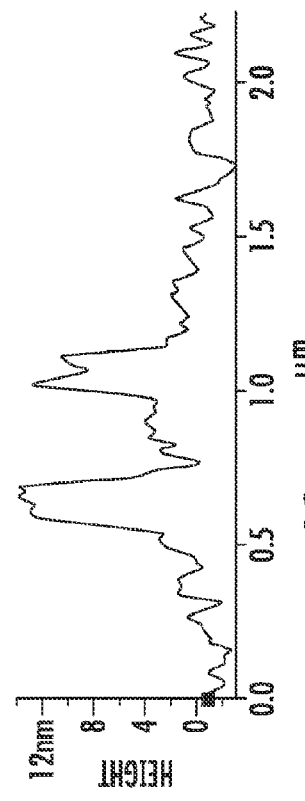
FIGS. 6A-6H show an atomic force microscopic characterization of a tCNTA.
Figure 6D:
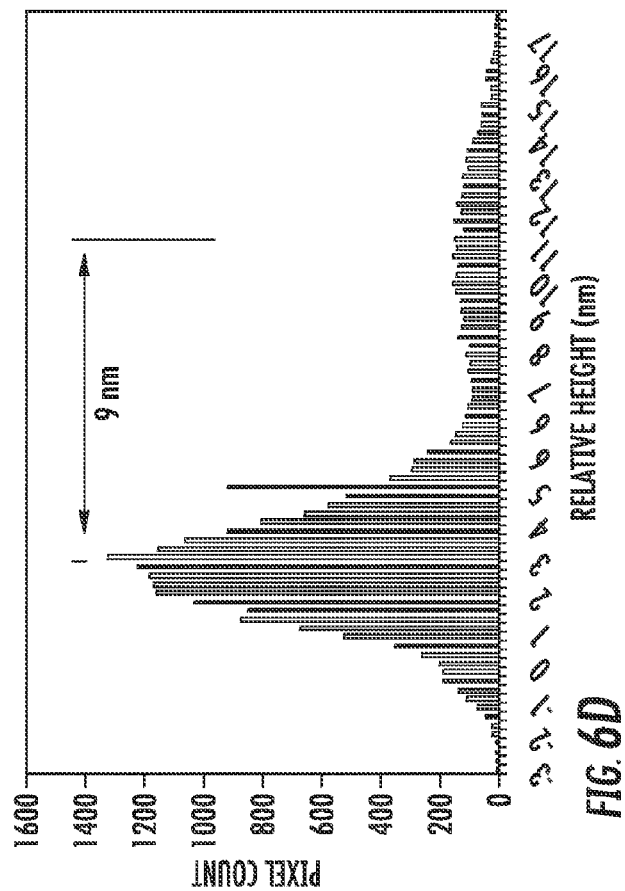
Figure 6A:
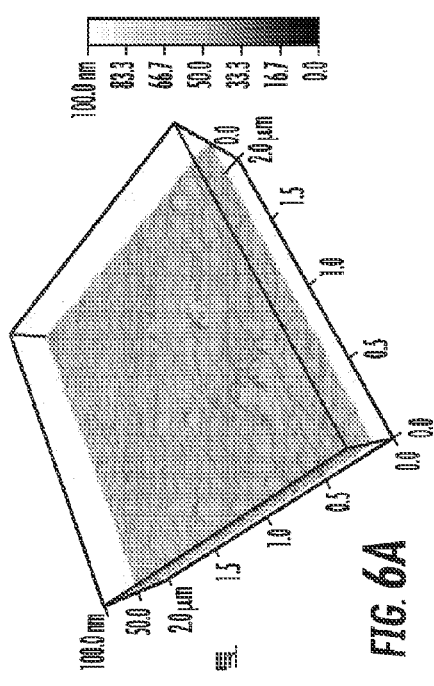
Figure 6B:
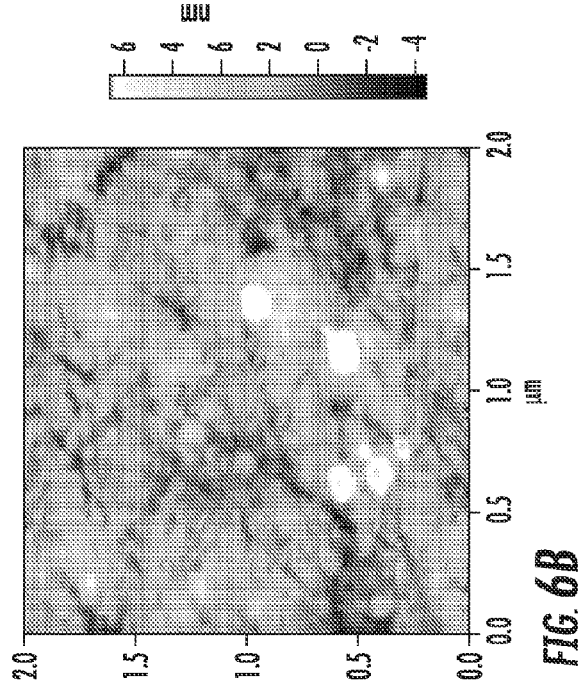

FIGS. 6A-6H show an atomic force microscope (AFM) characterization of a tCNTA embedded in a protective SU8 material e.g., of the type shown in FIG. 2A above. FIG. 6A displays the surface landscape on an as-polished carbon nanotube tip array (tCNTA) with no PPn coating obtained by the tapping mode scanning of an AFM. FIG. 6B is a plot of surface height of the same area as shown in FIG. 6A. The bright dots correspond to the height of the polished CNTs. In the example shown, the various progress rates of CNT growth and the filling SU8 in which there CNTs are embedded resulted in the different heights. FIG. 6C shows the cross section along the X'd line in FIG. 6B. As show, the height of CNT tips protruding out of the SU8 surface is about 9 nm. FIG. 6C shows the distribution of pixel heights in FIG. 6B. The two peaks are corresponding to the average heights of SU8 surface structures and the CNT tips. The typical height of CNT tips is indicated by the distance between the two peaks, which equals to 9 nm.

Figure 6G:
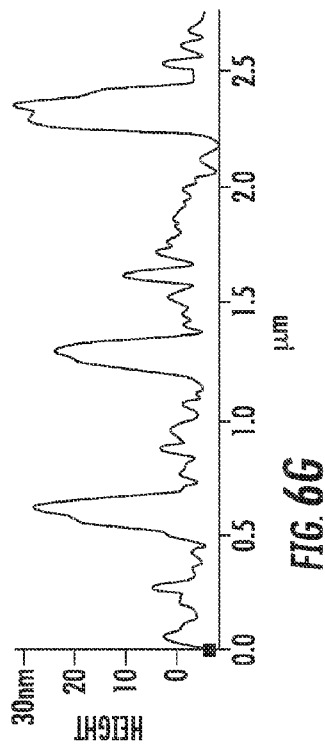
Figure 6H:
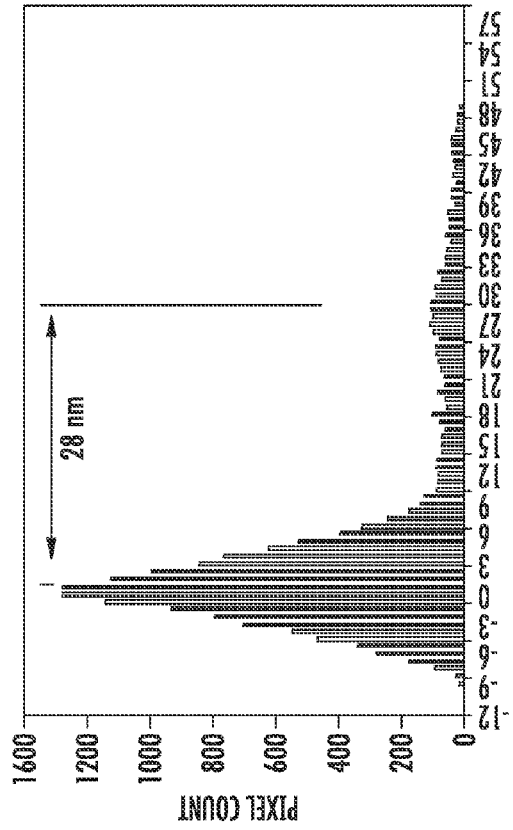
Figure 6E:
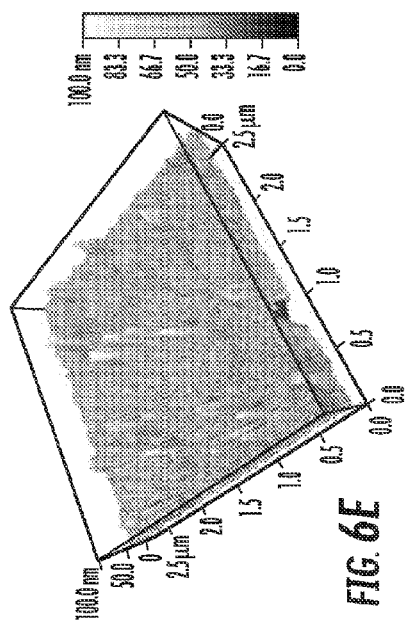
Figure 6F:
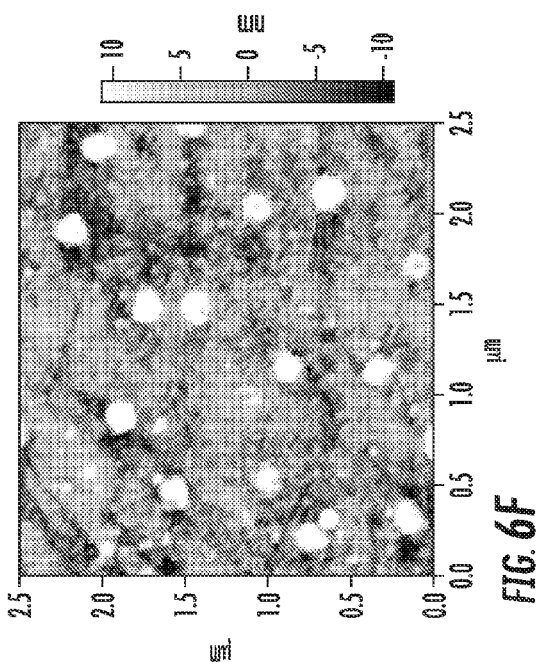

FIG. 6E displays the surface landscape on an as-polished carbon nanotube tip array (tCNTA) with a ferritin entrapping PPn coating obtained by the tapping mode scanning of an AFM. FIG. 6F is a plot of surface height of the same area as shown in FIG. 6E. The bright dots correspond to the height of the PPn coated tips of CNTs. FIG. 6G shows the cross section along the X'd line in FIG. 6F. As show, the height of coated CNT tips protruding out of the SU8 surface is about 9 nm. FIG. 6G shows the distribution of pixel heights in FIG. 6F. The two peaks are corresponding to the average heights of SU8 surface structures and the CNT tips. The typical height of CNT tips is indicated by the distance between the two peaks, which equals to 28 nm.

Taking the results of the above AFM measurements together, in this embodiment, the average thickness of PPn coating is about 9 nm, in agreement with observation with TEM.

As will be understood by those skilled in the art, in various embodiments, a variety of factors may determine the thickness of the MIP film 106. According to the mechanism of self-limiting coating processes, the thickness is determined by how fast the polymerization reaction can be stopped by the insulation of electrode. So the MIP resistivity, porosity, oxidation voltage, polymerization level, and the distribution of electric field etc can contribute to the thickness determination. Various embodiments described herein use cyclic voltammetry for the deposition. In such cases, the reaction rate in the polymerization may affect the density of the MIP film, therefore change the resistivity of the coating. In some embodiments, the nature of the electrode material used in the electropolymerization process may have significant influence on the anodic oxidation. Metals such as copper, nickel, chromium, platinum, gold, zinc and titanium typically exhibit different values of potentials of oxidation. For example, oxidation of phenolic monomer occurs more readily on the surfaces of noble metals such as platinum and gold. Similarly, carbon or functionalized carbon surfaces may prime the oxidation differently, so that the PPn film formation may happen in different fashion than metal surfaces. In some embodiments, one may utilize surface chemistry to modify CNT, e.g. with amine, carboxyl, or carbonyl groups, or to generate more defects in the carbon surface. The reactive sites and their densities on CNT may contribute differently to the polymerization.

Figure 8:
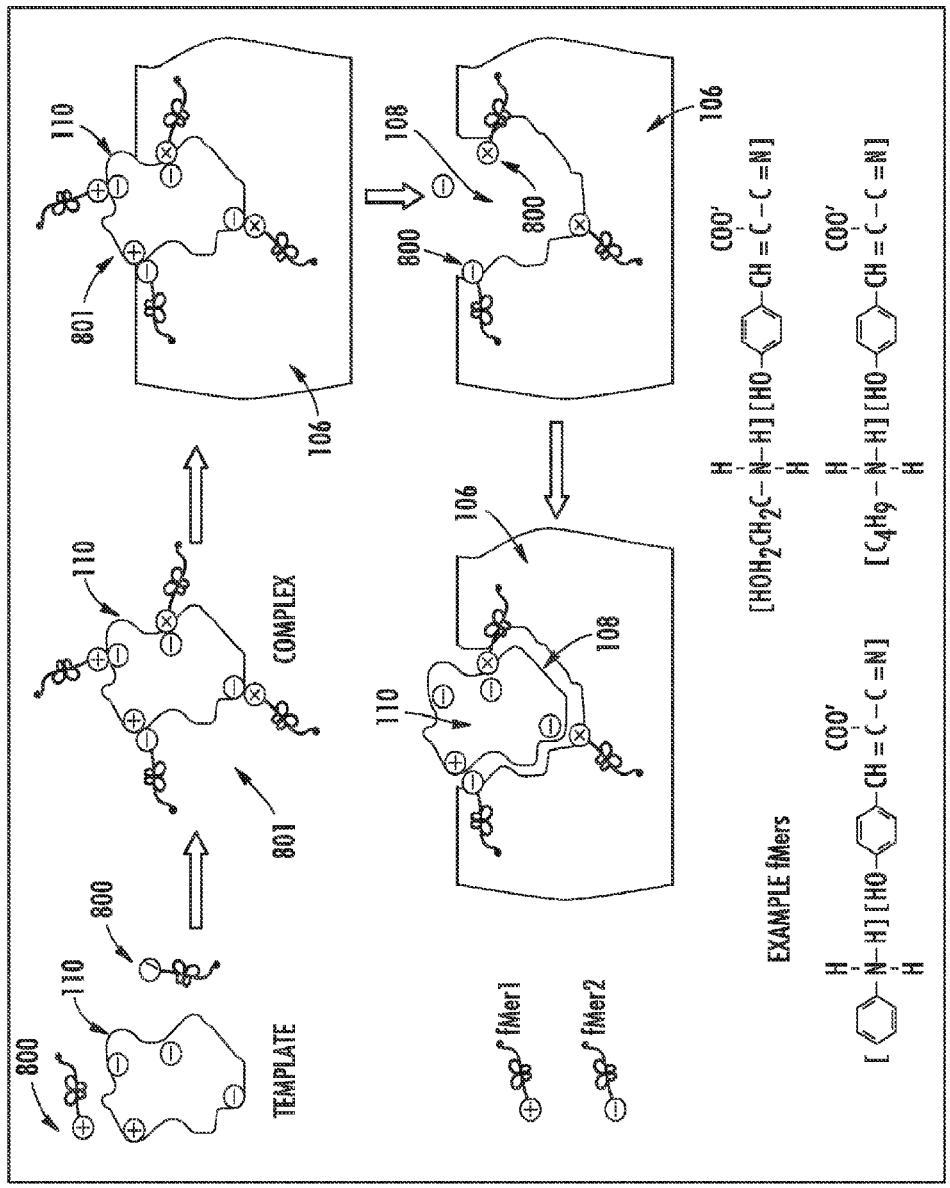
FIG. 8 illustrates a molecular imprint polymerization process featuring the use of functional monomers (fMERs)

Referring to FIG. 8, in some embodiments, one may facilitate imprint stability and specificity in the MIP film 106 by using designed cross-linking monomers (cMer) and functional monomers (fMer) in the electropolymerization process. Generically, molecular imprint of synthetic polymers is a process where functional and cross-linking monomers are co-polymerized in the presence of the template proteins or other molecules (i.e. the target molecules 110).

The functional monomers initially form a complex 801 with the protein target molecule 110 and, following polymerization, their functional groups are held in position by the highly cross-linked polymeric structure of the MIP film 106. The template molecule can then be dissolved to reveal the imprint binding site cavities 108 that are complementary in size and shape to the templates.

In the previously presented examples (e.g. as shown in FIGS. 2 and 2A), the target protein 110 was simply entrapped in the PPn coating 106 without the assist of fMers. In such cases the only specific information of the template protein being imaged on the imprint cavity 108 was the protein morphology. In order to improve the specificity, one can introduce a functional monomer to the deposition system or design a cross-linking monomer that has certain side-groups. One strategy is shown in FIG. 8. The fMer molecule 800 is made "sticky" to form H-bonds or to exert electrostatic attraction etc. in one end, while another end is made reactive to form covalent linkage during the electropolymerization. For example, several ionic liquid molecules listed in FIG. 8 have a negative charged carboxyl group and a phenolic group on each side respectively. Upon mixing with the target proteins 110, the pre-complex 801 will be formed after the fMers are adsorbed by the charged residues on the protein surface. In some embodiments, the phenol side will be left outside and can be linked to other polyphenols later when electropolymerization starts. Following the removal of proteins from the PPn coating, imprint cavities 108 with the fMer 800 decorations on their surfaces will exhibit more selectivity to the target proteins 110 because of the request of matching of the charge signature in the cavities 108. In other embodiments, a cross-linking monomer (cMer) branched by charged/polarized side groups may be used. For a given application, any suitable cMer know in the art may be used including: 3-nitrophenol, pyrogallol, 4-hydroxybenzenesulfonic acid, bromophenol blue, n-Aminophenol, 3-methyphenol, 3-nitrophenol, 1,n-dihydroxybenzene, 1,x,ytrihydroxybenzene, 5-amino-1-naphthalene, acetaminophen, poly(1,3-diaminobenzene), poly(p-chlorophenylamide), etc.

Referring back to FIG. 3, in some embodiments, the film 106 has a thickness which is relatively insensitive to voltammetry scanning rate of electropolymerization system 300. For example, as shown in the Table 1 below, for the PPn formation process described above, changing the voltammetry scanning rate between 20 and 100 mV/s may not significantly alter the film thickness.

TABLE 1

| Dopant | Dopant Free | | | $Na_2S$ |
|---|---|---|---|---|
| Scan rate (mV/s) | 10 | 50 | 100 | 50 |
| Thickness (nm) | 15 | 17 | 16 | 7.5 |

As illustrated in FIG. 2, the development of the MIP includes two major steps: (1) target molecule entrapment (e.g. in PPn); and (2) target molecule elusion from the entrapping layer.

A ferritin protein target molecule has a pI ~4.5, which means the protein carries positive charge at neutral buffer. When mixed with phenol deposition buffer, ferritin will be attracted to anode and co-deposition on the anode, i.e. the CNT sensor, surface with polyphenol.

Figure 7:
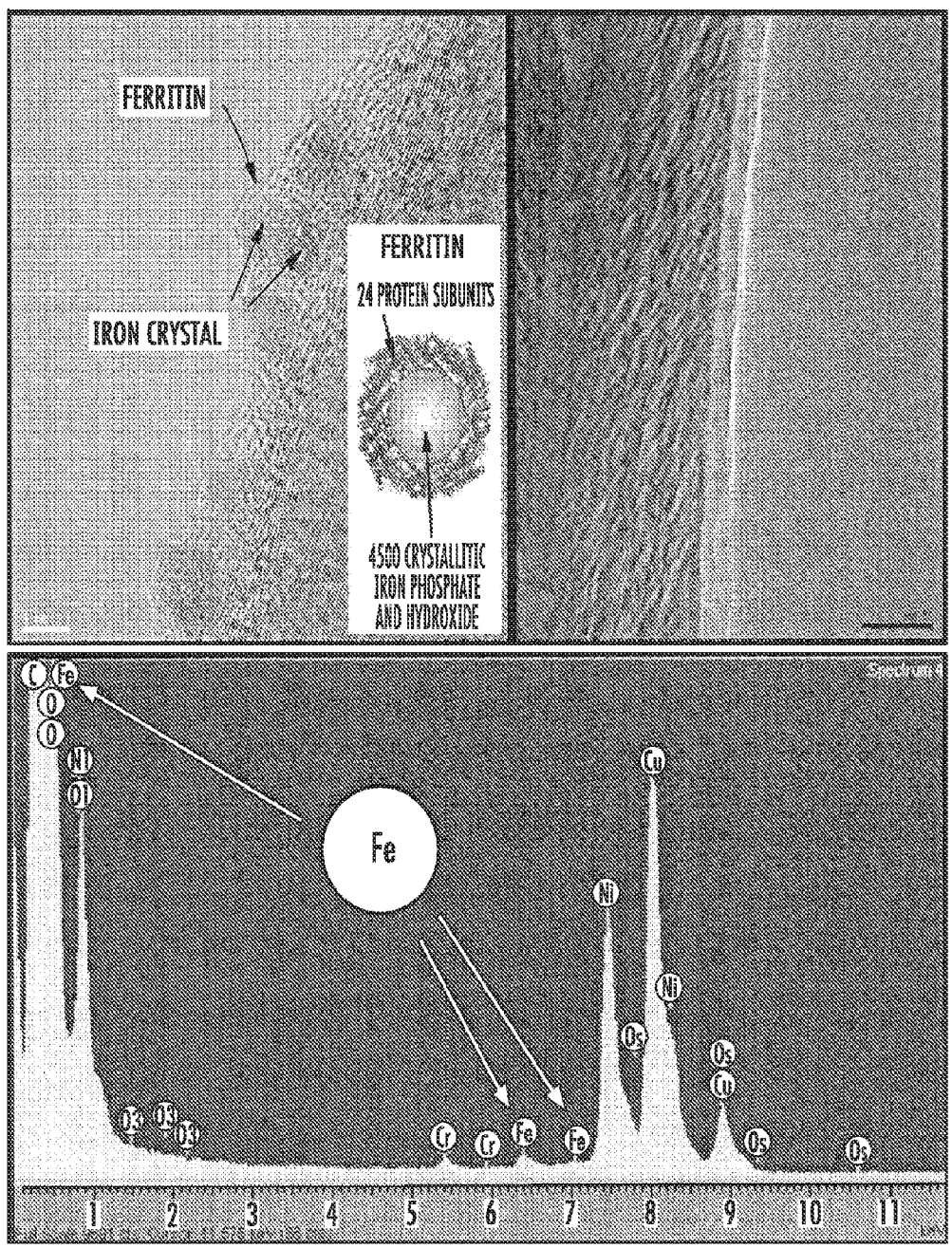

For example, the TEM image of FIG. 7 (top left) shows ferritin molecules immobilized on bare CNT surface by amide linkages formed between the free amines on ferritin and carboxyl groups on the functionalized CNT. The diameter of the iron crystal core in the ferritin molecule is around 5 nm. The TEM image of FIG. 7 (top right) shows ferritin entrapped in the PPn coating on CNT. The whole area of this image is subjected to energy dispersive spectroscopy (EDS) FIG. 7 (bottom) shows the results of the spectroscopy. The presence of ferritin is confirmed by the peaks of iron, which are not observed in the non-ferritin samples.

MIP target molecule elusion may be accomplished by washing the trapped molecules from the polymer layer. For example, in some embodiments, for protein removal, i.e. imprint development, a sensor with ferritin entrapped PPn coating may be rinsed and incubated overnight in deionized water (diW) at room temperature. Alternatively, a developing buffer containing 5% acetic acid and 10% sodium dodecyl sulfate (SDS) may be used instead of diW for higher protein extract efficiency. In such cases elusion may take place in about 1 hr, about 15 minutes, or even less. In other embodiments, PBS may be used as a developer, alone or in combination with diW.

Figure 9:
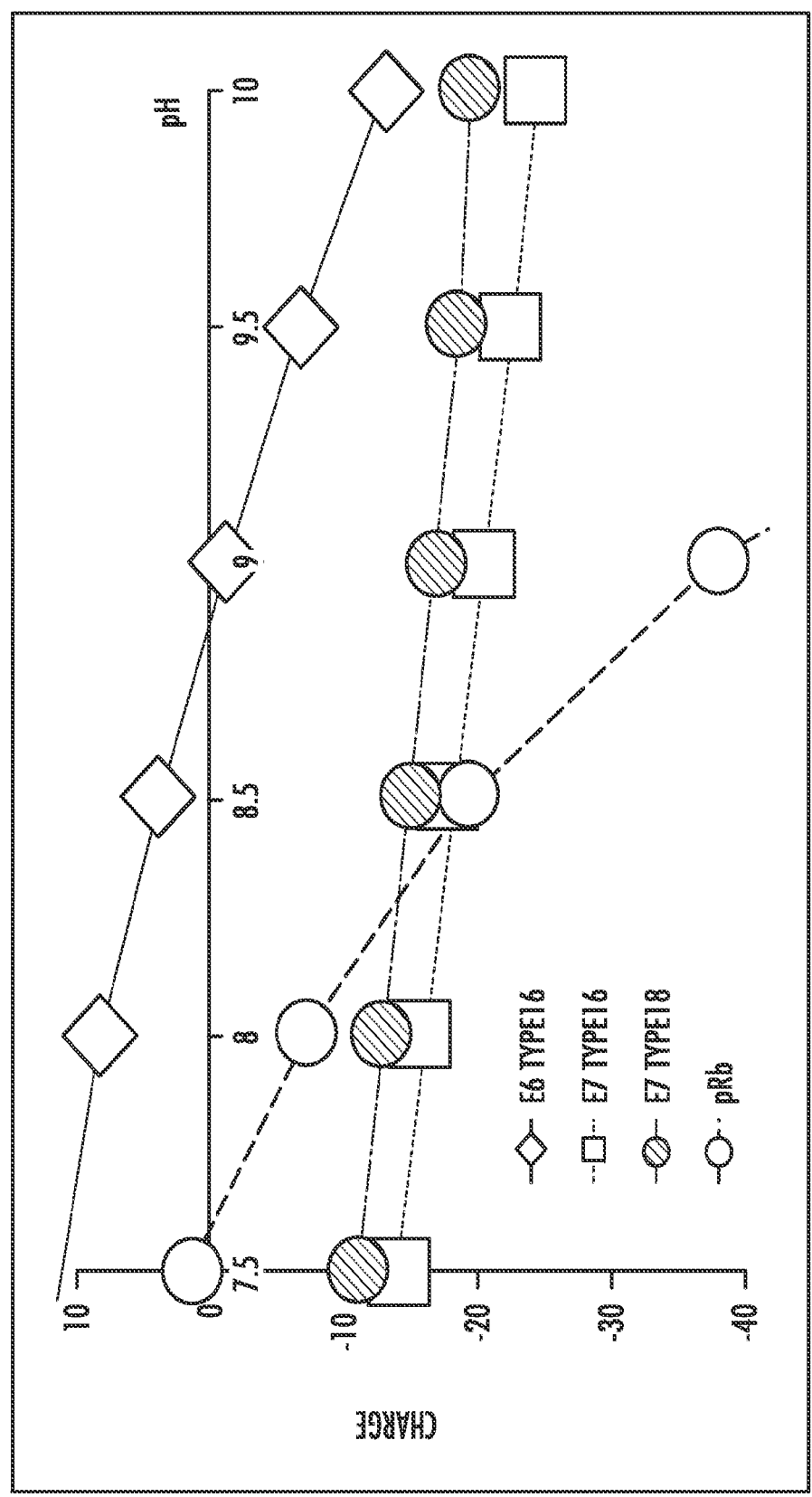
FIG. 9 is a schematic of a circuit for electrochemical impedance spectroscopy (EIS).

The development speed has been found to vary depending on the properties of the imprinted target molecule. Accordingly, in various embodiments, the imprint development protocol should be adjusted to match the properties of each kind of proteins that include size, surface charge, subdomain and subunits etc. FIG. 9 shows the theoretically calculated surface charge of several biomarker proteins as a function of pH. "E6 type16" carries positive charges at pH 7.5 to 9. But other three biomarkers "E7 type16", "E7 type18", and "pRb" are negatively charged at the same range. Therefore, more basic (pH>9) buffer solutions will be needed in order to have "E6 type16" showing the same result of a surface charge sensitive procedure as with other proteins. In some embodiments, it is important to record the buffer pH at which electropolymerization is conducted. The recorded pH needs to be used for biomarker rebinding buffer during a detection process. This may be especially important when fMers are used, since the charge profiles indicated by fMers in the imprints could be no longer matched to the protein surface at different pH.

In some embodiments, the removal of the template protein from the MIP nanocoating could be facilitated by purposeful adjustment of the pH. For example, if the electropolymerization is done at basic solution, then reducing pH could be helpful to facilitate the protein elusion by eliminating the electrostatic attraction between charged side residues of the proteins and the imprint cavities. In some embodiments, the effect of pH should take effect faster than any other elusion buffers because the nanocoating as a polymer network is more permeable to protons than other molecules. In this way, the time of harsh chemical treatments will be shortened, and consequently have the integrity of imprint structures better preserved.

In view of the above, it may be important to evaluate the imprint development and/or rebinding efficiency of a given device or process in order to optimize the performance of sensor 100. There are several ways to evaluate the imprint development and/or rebinding efficiency. As described in detail below, EIS can be used to monitor the progress of imprinting and rebinding etc. TEM can be used to assess protein entrapment as well. However, for many applications, protein molecules have too low contrast in compare with the polymer coating to be visualized. An exception is ferritin, which has an iron-crystalline core to differentiate itself from the adjacent materials under TEM.

Figure 10:
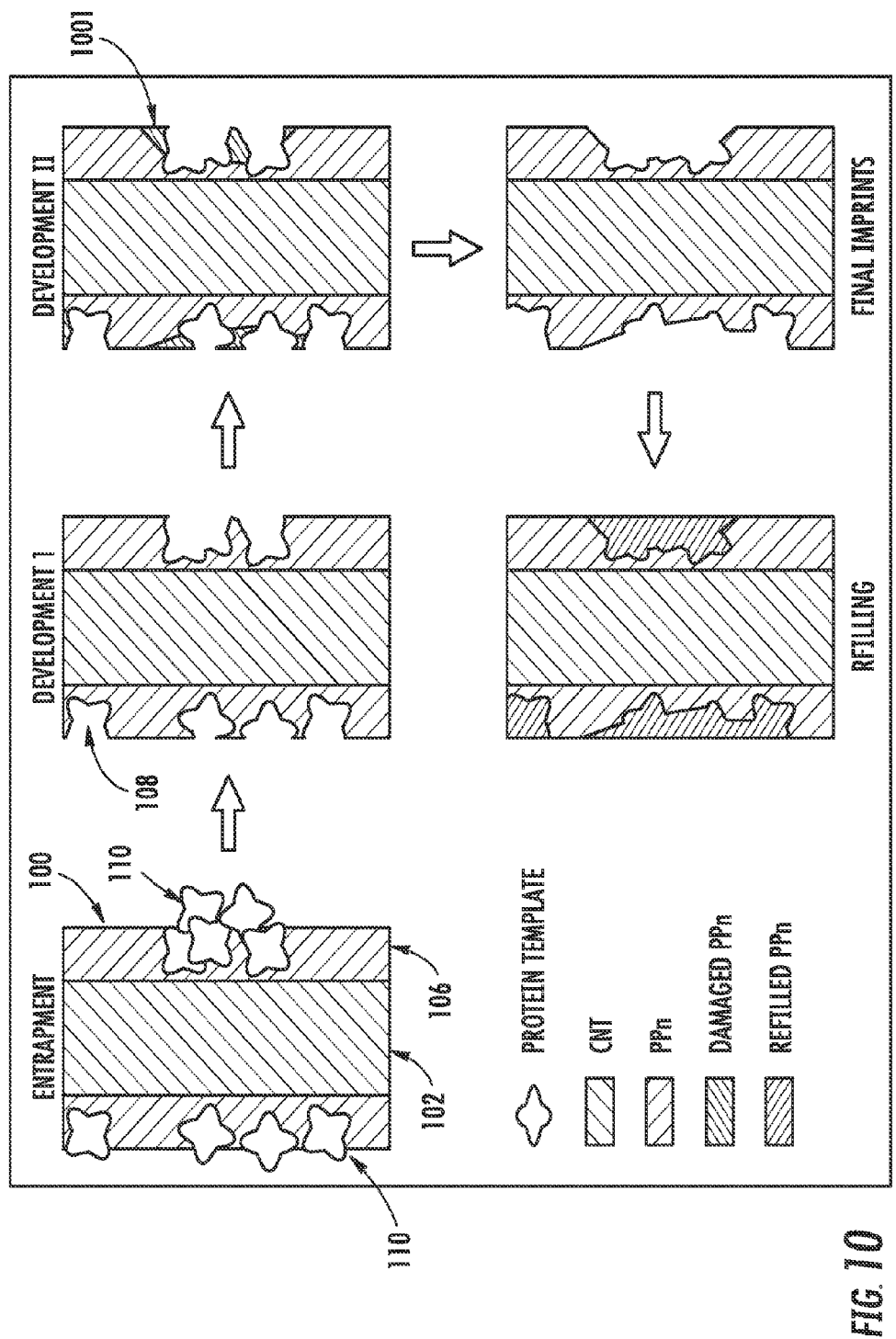
FIG. 10 illustrates a molecular imprint polymer film characterization technique.

In some embodiments, e.g. where TEM evaluation is impractical, the quality and amount of imprints can be measured using an imprint refilling method. For example, referring to FIG. 10, an MIP sensor 100 undergoes a second, post development electropolymerization with PPn so that PPn can fill in the imprint cavities 110. The volume of PPn that fills (Vrefill) the imprint can be calculated according to the charge generated at the refilling step. It can be converted to the amount of target molecule imprints 108. In one particular case of our preliminary studies, each CNT 102 may carry about 300 or more imprints. In fact, not all of the volume taken by the refilling PPn can be refilled by proteins. As illustrated in FIG. 10, Vrefill may also give an indication of the damage 1001 caused to MIP film 106 during the development processing. This information can be used to optimize the development process to reduce or minimize unwanted damage.

Detection

As noted above, using sensors 100 of the type described herein, the presence of a target molecule 110 may be detected by sensing a change in a physical property of the sensor's nanostructures 102 due to interaction of the MIP film coating 106 with target molecules 110.

For example, in some embodiments, the sensor may include a three terminal electrochemical cell of the type shown in FIG. 3. Electrochemical impedance spectroscopy (EIS) may be used to measure changes in the impedance of the electrochemical cell in response to the application of target molecules.

In one such embodiment, monitoring of the electrochemical behavior of the MIP thin-film may be conducted with a Reference 600 electrochemical system produced by Gamry Inc. (Warminster, Pa.), running under the control of Gamry Framework software. Data analysis is conducted with Gamry's Echem Analyst software. FIG. 11 shows an exemplary detection circuit for EIS. This EIS set up may be used to determine the impedance $Z_{cell}$ of the cell, and, in turn, to monitor for the presence of the target molecule.

Figure 12:
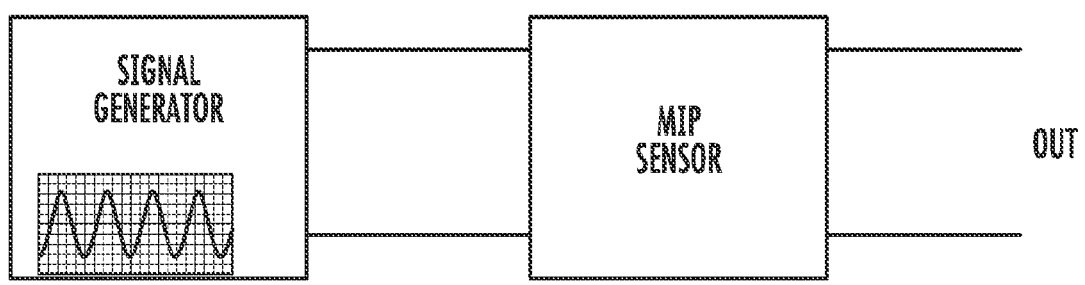
FIG. 12 illustrates an EIS characterization technique.

FIG. 12 illustrates an exemplary EIS analysis of an embodiment of a CNT array MIP sensor designed to detect the presence of ferritin. Electrochemical impedance spectroscopy (EIS) is conducted before and after PPn deposition to evaluate the impedance property of CNT array electrode surface and its interface to a surrounding buffer solution. The circuit is driven with a sine wave with a 10 mV of peak-to-peak amplitude. The sine wave is superimposed with a 300 mV DC voltage. The frequency of the sine wave is scanned from 1 Hz to 1 MHz.

During the measurement, ferrocene carboxylic acid is supplemented to the PBS buffer in which the sensor 100 is immersed at final concentration 1 mM. The impedance data are fitted to an electrical equivalent circuit using the impedance analysis function in the Gamry Echem Analyst software. The equivalent circuit provides an electrical analogue of thin film coating and chemical/physical processes. Mono-frequency (e.g. without frequency scanning) EIS is also used to monitor the protein binding dynamics. In this case, sine wave and DC voltage remained the same as that of frequency scanning.

FIG. 13A shows Nyquist plots of real and imaginary impedance resulting from EIS of the nanosensor 100. As described above, frequency is scanned from 1 Hz to 1 MHz. Three bold traces represent sensors of bare CNT (no PPn), with ferritin entrapped in the PPn film (PPn+Frtn) and imprints formation after the ferritin removal (Imprinted PPn). The other traces represent measurements taken with the sensor immersed in a buffer solution having ferritin present at different concentrations ($10^{-12}$, $10^{-11}$, $10^{-10}$, $10^{-9}$, $10^{-8}$, and $10^{-7}$ g/L). Note that the Nyquist plot for ferritin concentrations of $10^{-12}$ g/L can be clearly distinguished from the plot corresponding to no ferritin. This indicates that the presence of ferritin can be detected at concentrations on the order of picograms per liter.

FIG. 13B shows protein dose responses in impedance and faradic current of the sensor in the presence of ferritin and, alternatively, in the presence of bovine serum albumin (BSA). Measurements are plotted for the ferritin concentrations listed immediately above. Measurements are plotted for the bovine serum albumin (BSA) at concentrations of $10^{-10}$, $10^{-9}$, $10^{-8}$, $10^{-7}$, $10^{-6}$, $10^{-5}$, $10^{-4}$ and $10^{-3}$ g/L. In the top panel, sensor impedances measured at 10 Hz are plotted. The dashed line indicates the initial impedance before BSA applications. Faradic currents obtained from differential pulse voltammetry (DPV) are shown in the bottom panel. Each method (mono-frequency EIS and DPV) shows similar dosage responses to BSA and ferritin respectively. However, as measured by either technique, BSA needs more than $10^6$ times higher concentration than ferritin to produce a similar change in the impedance. This demonstrates a high selectivity of the imprints to ferritin molecules.

This selectivity ensures that the sensor will be highly sensitive to the presence of the target model, and relatively very insensitive to other molecule types. Accordingly, the sensor is well suited for the detection of the target molecule, even in the presence of one or more types of "noise" molecules.

MIP Film Characterization

Figure 14A:
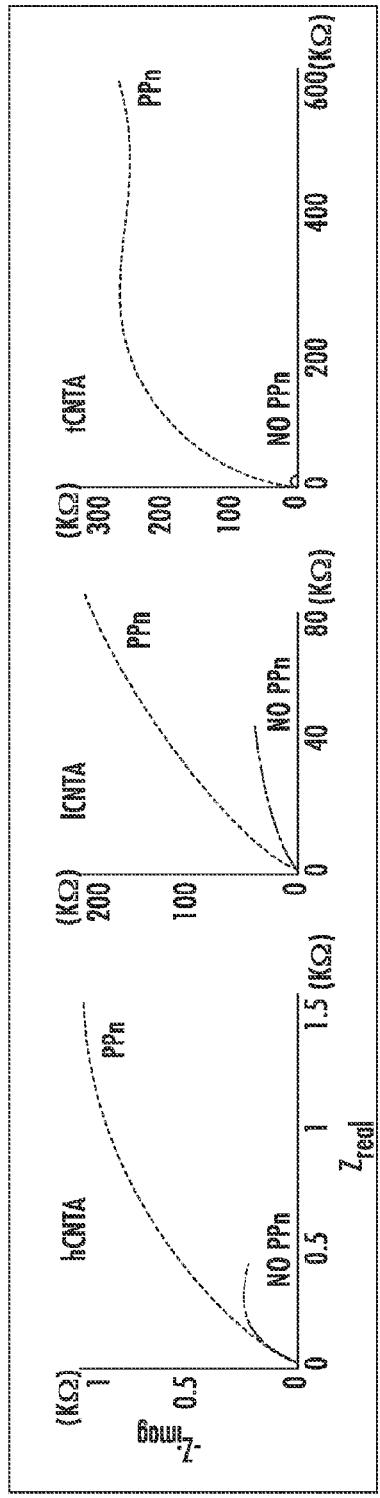
Figure 14C:
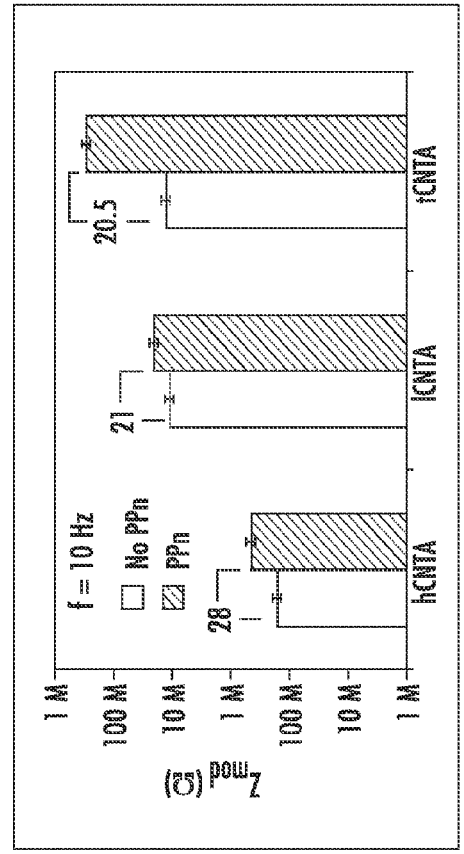
Figure 14B:
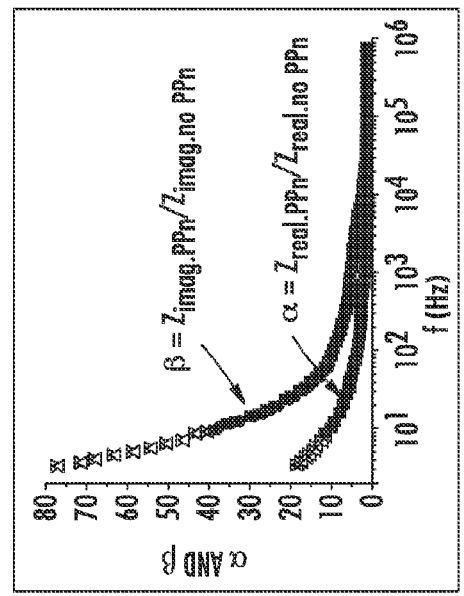

The EIS techniques described above may also be used to characterize MIP films deposited on the nanostructures. For example, FIG. 14 shows the results of EIS evaluation of the PPn coating on the different CNT array types (hCNTA, lCNTA, and tCNTA). FIG. 14A shows a comparison of Nyquist plots before (no PPn) and after PPn (PPn) coatings on the three CNT arrays. The frequency is scanned from 1 Hz to 1 MHz. FIG. 14B shows the complex impedance change of the tCNTA due to the PPn coating. The parameters α and β represent the multiple by which the real and imaginary parts of the impedance have been elevated by the presence of the PPn. Four separate recordings are superimposed. Two of the scans are started from 0.1 Hz, while the other two range from 1 Hz. FIG. 14C shows the impedance modes measured at 10 Hz before and after PPn coating for the CNT array types. The numbers above the columns denote the impedance ratio that is obtained by the impedance with PPn divided by the impedance without PPn.

The above evaluation demonstrates that PPn on CNT sensor can dramatically increase the impedance, especially at low frequency such as 3 Hz, where the $Z_{real}$ and $Z_{imag}$ are elevated nearly 20 (α) and 80 (β) times respectively for a tCNTA array as shown in FIG. 9B. Such an impedance difference offers a large dynamic range for detecting imprinting induced impedance change.

Figure 15:
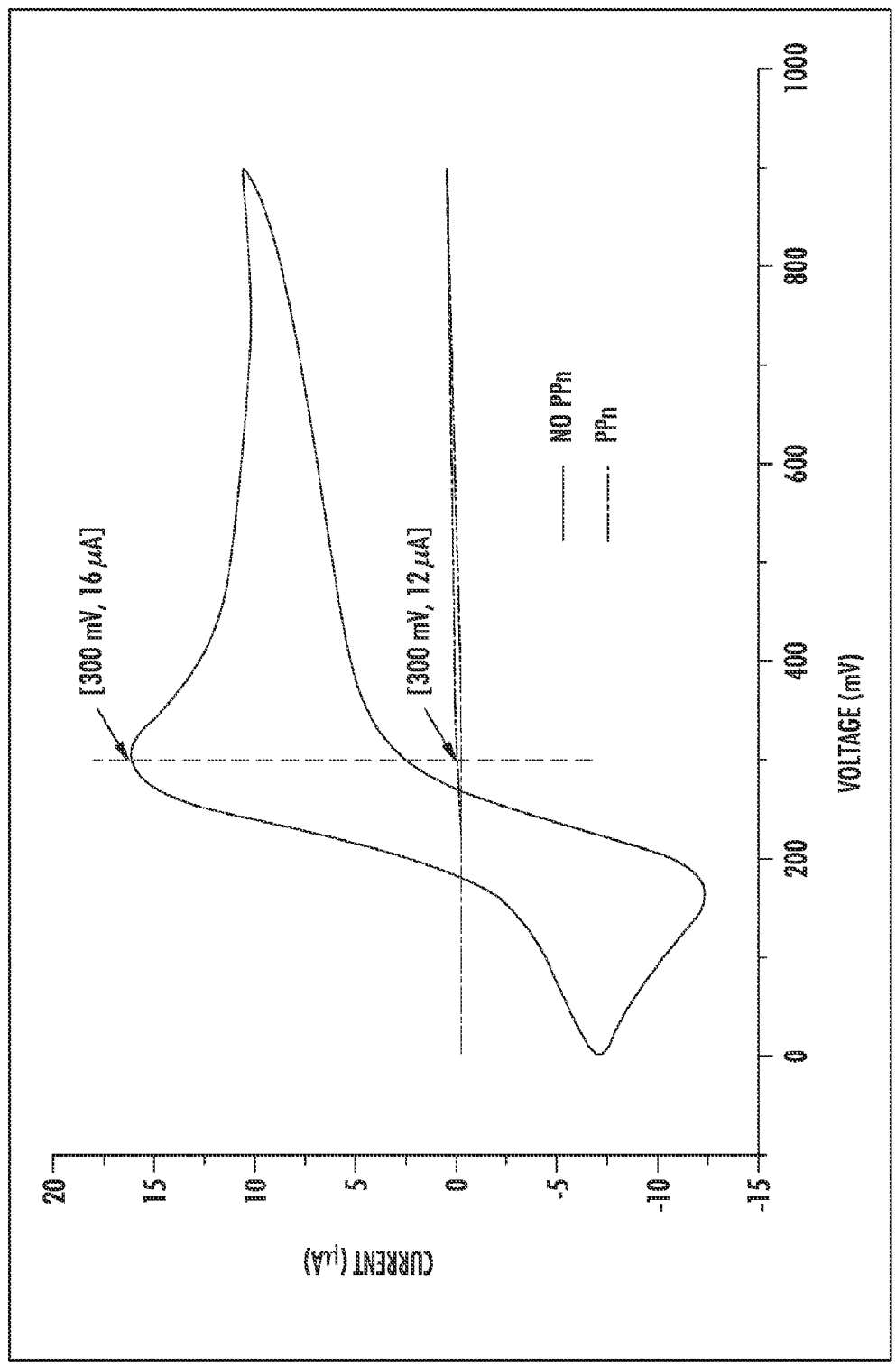
FIG. 15 is a voltagraph illustrating the impedance properties of a molecular imprint nanosensor.

PPn MIP film stability may be evaluated using cyclic voltammetry techniques of the type described above. For example, FIG. 15 shows a cyclic voltagram taken for a CNT sample (with and without PPn) immersed in a PBS buffer supplemented with ferrocyne carboxylic acid (FCA). As shown, the peak current is reduced by more than two orders of magnitude by the PPn film. Thus, the anodic peak current of the voltagram clearly serves an indication of the presence and integrity of the PPn coating.

Accordingly, measurement of the CV anodic peak may be used to explore f the stability of the PPn film under various conditions. For example, the tables below shows that PPn coating can dramatically reduce the FCA current from ~15 μA to nA or even pA range. Degradation of the PPn film under various conditions may be may be explored by measurement of increases of the measured peak current. For example, Table II shows exemplary peak current values for PPN coated CNT array samples immersed for various time intervals (0, 10, 20, and 30 min) in various organic solvents. For example, after exposure to methanol for 10 minutes, the peak current of Sample B increased in magnitude from 433 nA to −1.400 μA, indicating some degradation of the PPn film.

TABLE II

| | Peak Current | | |
|---|---|---|---|
| Sample | A | B | C |
| FCA before PPn | −16.83 μA | −12.66 μA | −13.02 μA |
| FCA after PPn | −1.658 μA | −433 nA | −376.2 nA |
| Solvent | Methanol | Ethanol | Acetone |
| FCA after 10 min | −8.457 μA | −1.400 μA | −1.164 μA |
| FCA after 20 min | — | −800 nA | −1.331 μA |
| FCA after 30 min | — | — | −1.405 μA |

Similarly, the Table III shows exemplary peak current values for a PPN coated CNT array sample baked on a hot plate for 10 minutes at various temperatures (40, 60, 80, and 100° C.). note that heating results in only a modest increasing in peak current, indicating that the PPn film is relatively stable under these thermal conditions.

TABLE III

| Sample C | Peak Current | | |
|---|---|---|---|
| FCA after PPn | −706.2 nA | −730.1 nA | −641.0 nA |
| FCA after 10 min at 40° C. | −717.2 nA | −742.3 nA | −737.7 nA |
| FCA after 10 min at 60° C. | −741.5 nA | −744.7 nA | −798.5 nA |
| FCA after 10 min at 80° C. | −661.1 nA | −699.8 nA | −791.5 nA |
| FCA after 10 min at 100° C. | −638.6 nA | −683.2 nA | −773.7 nA |

Table IV shows exemplary peak current values for PPN coated CNT array samples incubated in buffers supplemented by surfactants of various types (SDS, Tween-20, NP-40, and Triton x-100) for various times.

TABLE IV

| | Peak Current | | | |
|---|---|---|---|---|
| Sample | A | B | D | C |
| FCA before surfactant | −148.1 nA | −6.260 nA | −4.125 nA | −6.445 nA |
| Surfactant | SDS (1%) | Tween-20 ( | NP-40 (1%) | Triton x-100 |
| FCA after 1 hr | −4.532 nA | −1.827 nA | −199.2 pA | −2.315 nA |
| FCA after 8 hrs | −76.37 nA | −115.5 nA | −136.6 nA | −1.047 nA |
| FCA after 12 hrs | −300.0 pA | −18.21 pA | −1.860 nA | −173.0 pA |
| FCA after 24 hrs | −7.537 nA | −1.475 nA | −898.5 pA | −13.88 nA |

Table V shows exemplary peak current values for PPN coated CNT array samples incubated in buffers at a given pH range for various times. As shown, the pH range was measured at the various time intervals to detect and possible pH drift.

TABLE V

| Sample | Peak Current | | | |
|---|---|---|---|---|
| | A | B | D | C |
| FCA before pk | −121.0 pA | −837.2 pA | −8.192 nA | −667.5 pA |
| pH at 0 hrs | 1.0-1.2 | 4.1-4.4 | 4.9-5.1 | 12 |
| FCA at 0 hrs | −3.346 μA | −81.96 pA | −675.1 nA | −344.6 nA |
| pH at 1 hr | 1.0-1.2 | 4.4 | 5.5.-5.8 | 11 |
| FCA at 1 hr | −6.757 μA | −762.2 nA | −673.7 nA | −696.5 nA |
| pH at 4 hrs | 1.0-1.2 | 4.4 | 5.5-5.8 | 11 |
| FCA at 4 hrs | −1.149 μA | −794.5 nA | −689.2 nA | −836.0 nA |
| pH at 12 hrs | 1.0-1.2 | 4.4-4.8 | 5.8 | 9-10 |
| FCA at 12 hrs | −1.707 μA | −855.0 nA | −688.5 nA | −867.5 nA |

Figure 16:
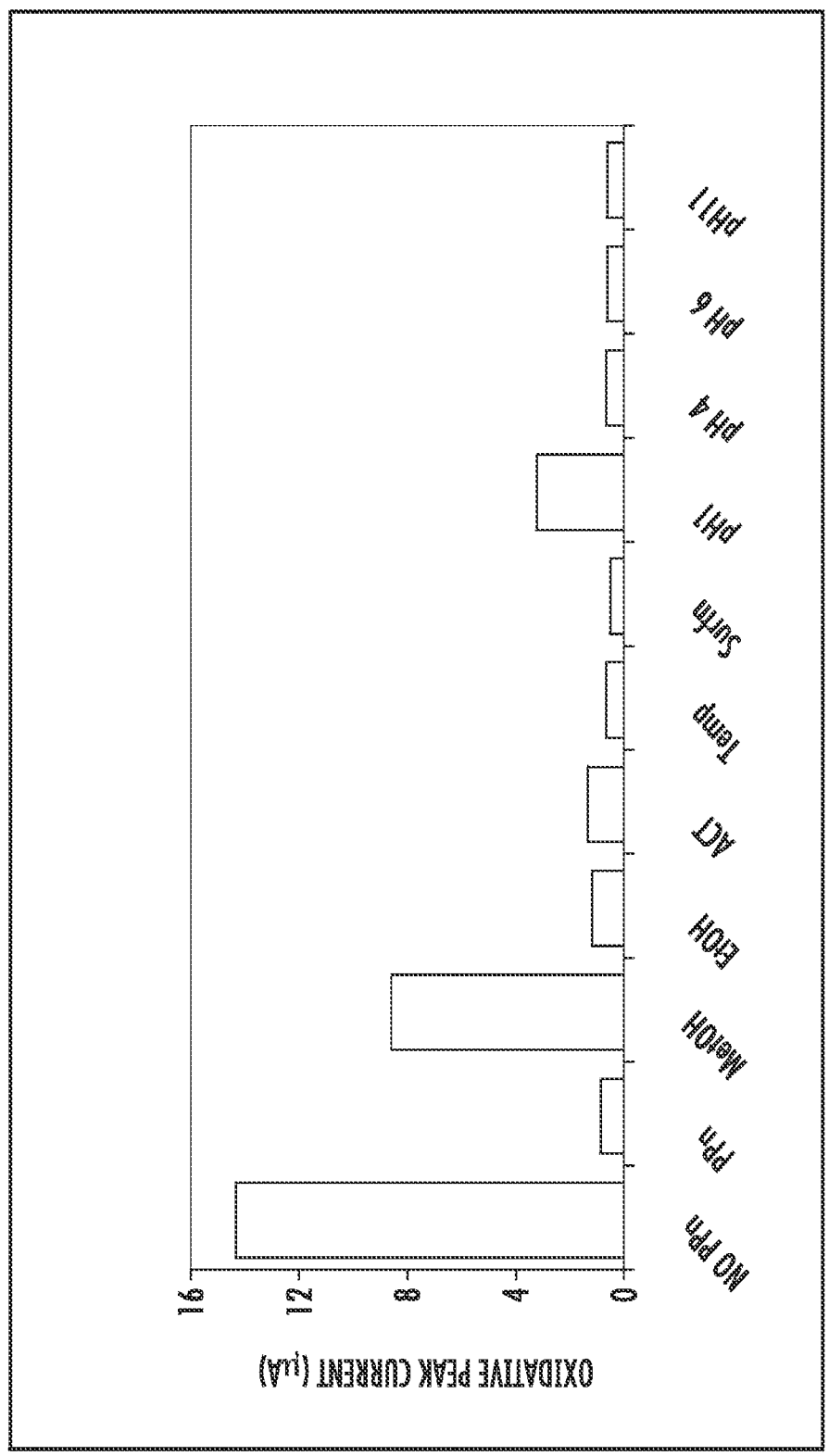
FIG. 16 illustrates the stability of a molecular imprint polymer film under various conditions.

Similarly, FIG. 16 summarizes the effects of organic solvents, temperature, surfactants and pH on PPn stability were presented based on the peak current of CV.

The above measurements demonstrate that PPn films exhibit good thermal stability at the testing conditions. The PPn remains stable in contact with different kinds of surfactants including ionic (SDS) and non-ionic (Tween 20, Triton x-100 and NP-40) ones. Some organic solvents (methanol) and pH (acidic) may lead to some changes in the FCA currents, Alternate Sensor Embodiments The examples of sensor 100 above feature MIP layers 106 on vertically aligned CNT arrays. However, it is to be understood that sensor 100 may include other types of MIP coated nanostructures. The nano structures may include nanowires, nanorods, nanoparticles, nancones, etc. Nanostructures 102 may be made of any suitable material including metals (Au, Ag, Ti, Mo, metal alloys, etc.), semiconductors such as Si (doped or undoped), conductive polymers, a conductive oxide (e.g. ZnO) etc. The nanostructures may be arranged in any geometry including regular arrays, irregular arrays, random arrays. The nanostructures may be vertically arranged (i.e. extending perpendicular to a substrate), horizontally arranged (i.e. extending parallel to a substrate), or arranged at any intermediate angle.

In one embodiment, the sensor 100 includes a mesh of conductive nanotubes or nanowires (a "nanomesh") coated with an MIP film 106. In some embodiments, the mesh may lay substantially flat on an underlying substrate 104. As with CNT's the electrical properties (e.g. impedance) of the mesh changes in the presence of a target molecule 110 having a shape corresponding to that of imprinted cavities 108 in the MIP film 106.

In another embodiment, the sensor 100 includes one or more graphene sheets with an MIP film 106, e.g. formed on a silicon substrate 104. As with CNT's the electrical properties (e.g. impedance) of the coated graphene sheets changes in the presence of a target molecule 110 having a shape corresponding to that of imprinted cavities 108 in the MIP film 106.

In another embodiment, the sensor 100 includes an array of Si nanowires coated with MIP film 106. As with CNT's the electrical properties (e.g. impedance) of the coated nanowire array changes in the presence of a target molecule 110 having a shape corresponding to that of imprinted cavities 108 in the MIP film 106.

Field Effect Transistor Based Nanosensor

Figure 17:
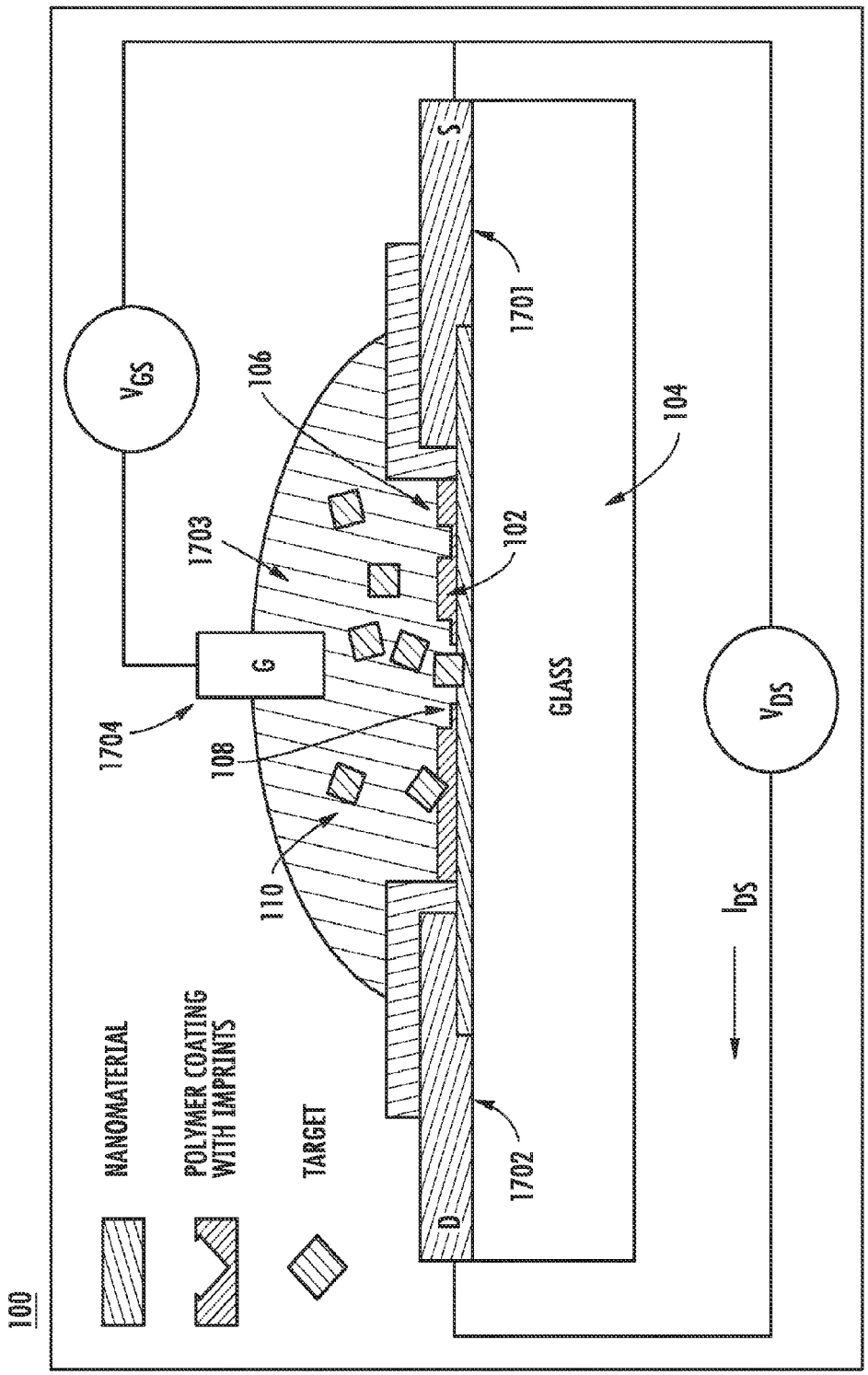
FIG. 17 is a schematic of a field effect transistor sensor.

Referring to FIG. 17, in some embodiments the sensor 100 is arranged as a field effect transistor (FET). As shown, a nanostructure 102 (e.g. a nanotube, nanowire, nanomesh, graphene sheet, nanowire array, etc) is located on glass substrate 104. The nanostructure 102 is coated with an MIP layer 106, and is disposed between source and drain electrodes 1701, 1702. A sample buffer 1703 is located over the MIP layer 106, and is in electrical contact with gate electrode 1704. As in previous example, the electrical properties (e.g. impedance) of the coated nanostructure 102 changes in the presence of a target molecule 110 having a shape corresponding to that of imprinted cavities 108 in the MIP film 106. Accordingly, the behavior of the FET will differ in the presence of the target molecule 110. In one embodiment, the voltage difference between the gate electrode 1704 and the drain electrode may be varied while the source-drain current is measured. The presence of the target molecule 110 will register as a change in the relationship between the gate voltage and the source/drain current.

Integrated Nanosensors

In some embodiments one or more sensors 100 may be integrated in a single device. When a plurality of the sensors 100 are used, different sensors 100 may be imprinted to detect different target molecules 110.

Figure 18A:
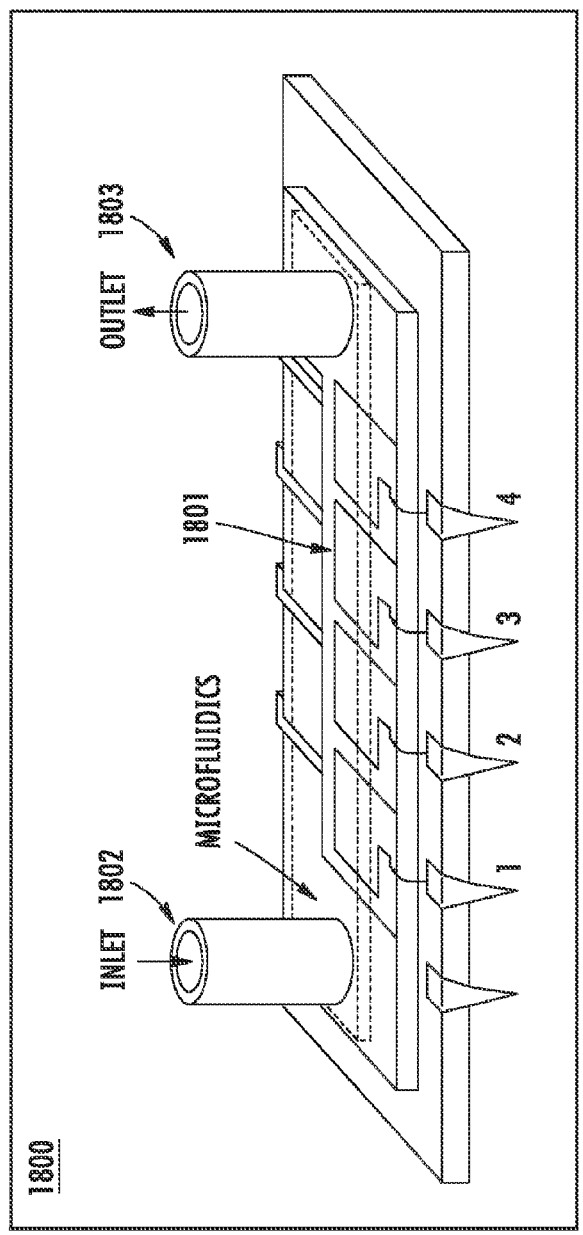
FIG. 18A is a schematic of an integrated nanosensor device.
Figure 18B:
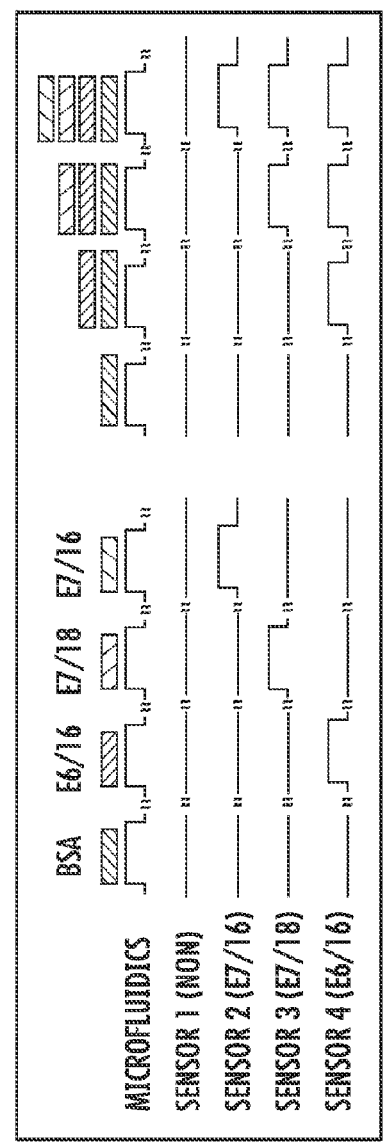
FIG. 18 B illustrates the operation of the device of FIG. 18A.
FIGS. 18C and 18D are schematics of integrated nanosensor devices.
Figure 18C:
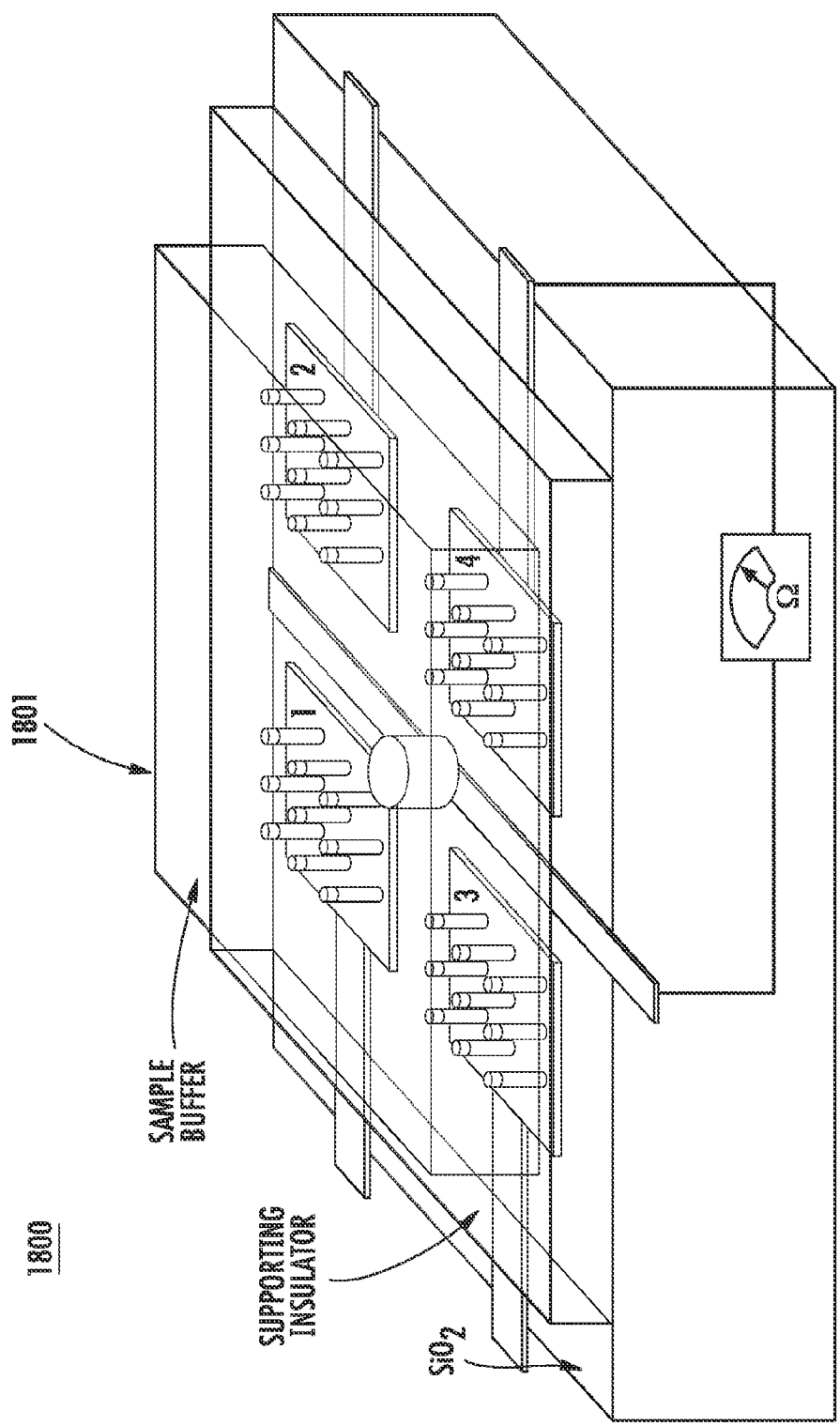

For example, referring to FIGS. 18A and 18B, integrated sensor device 1800, includes MIP sensors labeled 1, 2, 3, and 4. Sensor 1 is a control which has not been imprinted with a target molecule. Each sensor of sensors 2, 3, and 4 has been imprinted with a different target molecule (proteins E7 type 16, E7 type 18, and E6 type 16, respectively). Each sensor may be independently addressed by a corresponding set of electrodes to provide a signal indicative of the presence of the corresponding target molecule. For example, one or more sensors may be independently addressable by an EIS detection system as described above. In some embodiments, one or more sensors may be an independently addressable FET sensor of the type described above.

Samples to be tested may be introduced to the sensors via a microfluidic channel 1801 having an inlet 1802 and an outlet 1803. The channel may include one or more microfluidic elements to control the flow of sample to the sensors. The use of micro fluidics allows for highly sensitive control over the sample flow rate.

FIG. 18B illustrates the electrical response of the sensors to serial and parallel application of sample fluids including the various the target molecules. As shown, the sensors can output unique signals indicative of the presence or absence of each target molecule, either alone or in combination.

In one embodiments, the sensors are fabricated on a silicon substrate. Each sensor may be very compact, e.g. about 1 square millimeter or less. In some embodiments, the sensors may be fabricated as follows. The different target molecules may be separately prepared in a single kind of electropolymerization buffer. By switching buffer inputs and electrical active terminals, each target molecule may be selectively deposited to the designated sensor unit. Then the entire device 1800 may then be rinsed with the protein removal buffer (or imprint developer) to reveal the imprints and make the sensor functionally available.

Figure 18D:
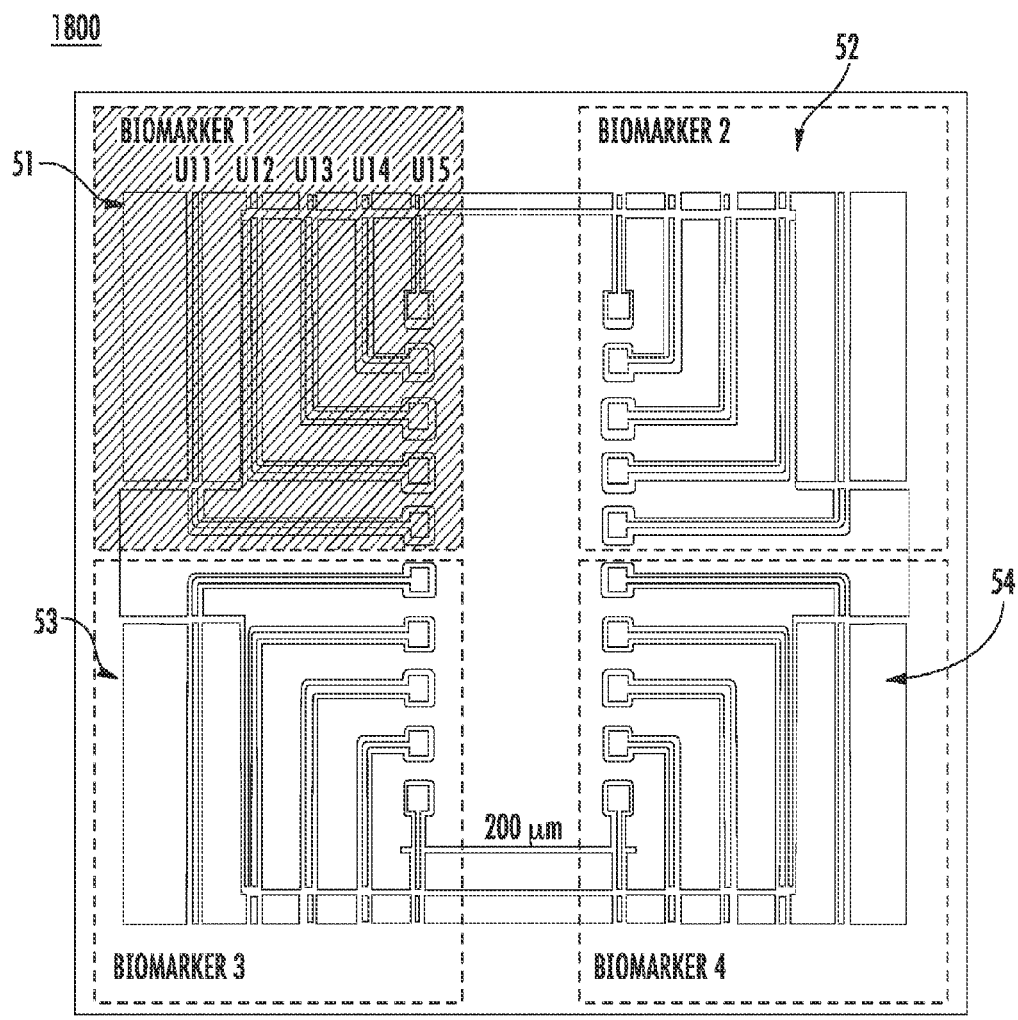

FIG. 18D shows an alternate embodiment of the integrated sensor device 1800 featuring four sensors S1, S2, S3, and S4, each of which includes five sensors imprinted with a respective target molecule. The sensors are formed on a SiC coated Si wafer. Electrodes (e.g. ti electrodes) for each sensor (e.g. electrodes labeled U11-U15 corresponding to the five sensors is the set S1) are patterned on the SiC surface.

Integrated sensors of the type described above may be fabricated using any suitable technique know in the art, including photolithographic techniques, micro-electromechanical system (MEMS) fabrication techniques, etc.

Biomimetic Sensor

Figure 19:
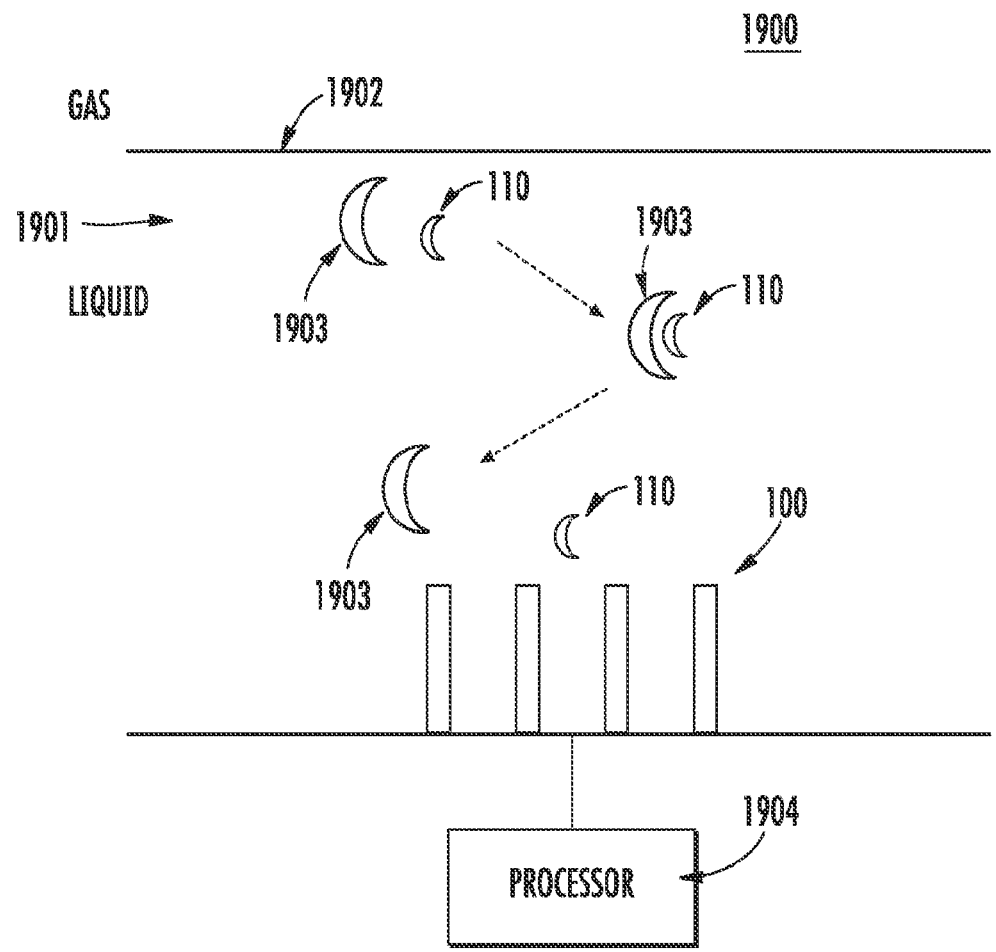
FIG. 19 illustrates a bio-mimetic sensor system.

The inventors have realized that sensor system designs may be based on naturally occurring sensory organs, e.g. insect olfactory organ (e.g. the sensory hair on a silkworm antennae). For example, referring to FIG. 19, a bio-mimetic sensor system 1900 includes a one or more (e.g. an array of) MIP coated nanostructure sensors 100 of the type described above. As above, the MIP sensor is imprinted with a target molecule 110 in order to provide sensitive and highly selective detection of the target molecule 110. The MIP sensor 100 thus operates in a manner similar to the olfactory receptors in an insect olfactory organ.

The MIP sensor 100 is immersed in a thin layer of liquid 1901 (or other fluid or gel) with a gas liquid interface 1902. This liquid layer mimics the sensillar lymph surrounding the neuronal dendrites in an insect sense organ.

The liquid interface 1902 may be covered with a gas permeable membrane which allows the target molecule 110 to permeate through the membrane into the liquid. This membrane mimics the cuticle of the insect organ. The membrane may be hydrophobic, and thus relatively impenetrable by liquids. Examples of gas permeable membranes include macroporous polytetrafluorethylene (PTFE) and silicone rubber.

Binding agents 1903 are present in the liquid which mimic pheromone-binding-protein found in insect olfactory organs. The binding agent molecules 1903 selectively bind to target molecules 110 which have diffused into the liquid. Once bound, the target molecules 110 are carried in the direction of the MIP sensor 100. Once in proximity to the MIP sensor 100, the binding molecules 1903 release the target molecules. For example, the binding molecules 1903 may dissociate with the binding molecule in response to a controlled pH in the vicinity of the MIP sensor 100.

Sensors of this type have a number of applications, including chemical detection, such as explosive detection. Target molecules 110, which may have a very low concentration, diffuse across the membrane and are directed by the binding agents to concentrate in proximity to the MIP sensors 100. Processor 1904 can monitor the signals from sensor 100 to determine the presence and/or concentration a target molecule. When the concentration near the sensor 100 becomes greater than the minimum sensitivity of the sensor 100, indicating the presence of the target molecule 110, the processor 1904 may trigger an alarm or provide another suitable output. For example, in one embodiment, the sensor system may be used to inspect cargo or luggage for the presence of trace amounts of an explosive, such as trinitrotoluene.

Processing and Analysis

Any of the sensors described herein may feature a monitor or analysis processing unit which receives signals from the MIP sensor indicative of the presence of the target molecule. The signals may be analyzed, e.g., by a digital computer. The computer may output information based on these signals, and/or control one or more other devices based on the analysis. For example, in an embodiment where the sensor system is employed to detect the presence of explosives, a signal indicative of the presence of an explosive chemical could trigger an alarm. In embodiments where the sensor system is employed to monitor a chemical process, a signal indicative of the presence of, or a certain concentration of, a target molecule could trigger an automatic modification on one or more of the processes parameters (e.g. temperature, pH, etc.). As will be understood by one skilled in the art, the sensor devices and techniques described herein can similarly be adapted to numerous applications.

Some embodiments may feature multiple MIP sensors, possibly fabricated to be sensitive to different target molecules. In such embodiments, a processor may analyze information indicative of the simultaneous presence and/or the relative concentration of multiple target molecules, and determine output or control actions based on this information.

Any of the analysis methods described herein can be implemented in hardware or software, or a combination of both. The methods can be implemented in computer programs using standard programming techniques following the method and figures described herein. Program code is applied to input data to perform the functions described herein and generate output information. The output information is applied to one or more output devices such as a display monitor, or may be used to automatically control one or more devices or systems. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

Example

Ultrasensitive Detection of Proteins

From disease diagnosis to laboratory proteomic study, monoclonal antibodies (mAbs) are one of the key elements for biorecognition; however, they are problematic due to their high cost, low stability, and compromised specificity. Polymeric molecular imprints (MI) could be used as artificial antigen receptors thereby replacing mAbs. However the progress towards an ultrasensitive imprinted sensor, particularly for proteins, has been fairly slow, although the technical concept was recorded thirty years ago. Here, we report our significant advance in an imprinted protein sensor, believed to be 104 times more sensitive than previous devices having e.g. minimum detectable human ferritin concentrations of 20 aM by electrochemical impedance spectroscopy. Further, using the devices and techniques described herein, robust selectivity may be demonstrated with other proteins, binary samples, and cellular protein extracts. Moreover, $Ca^{2+}$ induced calmodulin conformational change was sensitively detected. The molecular imprinted nanosensor affords sensitive antibody-free protein detection, and holds promise for applications in those instances where antibodies, aptamers, or natural ligands are not available, or where protein conformational changes reduce sensor functionality.

MI polymers may be used as bulky materials for chromatographic separations, antibody-free ligand-binding assays, and selective sample enrichment by solid-phase extraction. MI polymers may be applied as films on electrodes lacking nanostructures to detect small organic molecules. Protein imprinting strategies may be used as well. However, the detection limits of such techniques are typically on the μg/ml level, which are not comparable to the sensitivity of embodiments of the nanosensors described herein.

Not wishing to be bound by theory, this may be due, in part, to several factors: 1) the fragility and complexity of the protein molecules, which make them vulnerable to the imprinting chemistry; 2) MIP films on non-nano structures are too thick to exert remarkable signals corresponding to the targets, particularly when their concentrations are low; 3) the detection mechanisms do not allow for effective signal conversion of the target bindings; and 4) the basal sensor architectures are not supportive of highly sensitive detection.

In various embodiments, the nanosensor herein overcomes many of these obstacles, by imprinting a non-conducting polymer nanocoating on the tips of carbon nanotube (CNT) arrays, e.g. as described above. The protein of interest, or template protein, is initially incorporated within the nanocoating. Upon imprint development, i.e. removal of the proteins from the superficial part of the nanocoating, the sensor electrical impedance is greatly reduced due to electrical leakage through the surface voids left behind by the imprints in the nanocoating. Subsequent re-binding of the target protein into these voids is detected as an increase of impedance, due to the relatively lower conductivity of the target protein. The fabrication and detection procedures are illustrated in FIG. 2A, discussed in detail above. Notably, the nonconductive polymeric nanocoating was generated on CNT tips by electropolymerization of polyphenol (PPn). This self-limiting deposition process affords both convenience and highly conformal nanocoating with uniform thickness. Such nonconductive nanocoating was preferred to low noise recordings, and beneficial for highly sensitive detection. EIS measurements indicated that the PPn coating on the tips of the CNT arrays exhibited the highest impedance improvement among a variety of arrays. An additional reason to construct the sensor architecture with CNT tips was that electrochemical detection can be facilitated with faster electron transfer kinetics on nanotube tips than on nanotube side walls.

The embedded proteins on the outer surface of the PPn coating could be readily removed by sodium dodecyl sulphate (SDS)-supplemented phosphate buffered saline (PBS). The change in sensor impedance corresponding to the protein removal was measured by EIS. A subsequent refilling experiment of the type described above was conducted by electropolymerizing PPn into the voids of the post-imprinted sensor, to evaluate the number of potential imprint sites on the sensor. According to the total charge generated at the initial PPn coating (140 degrees C.) and at the refilled state (30 degrees C.), we estimate that the volume occupation of the imprints was about 21% of the total polymerized PPn. This charge could then be used to calculate the number of imprinted hFtn molecules. In one particular case, we calculated that each CNT carried ~300 hFtn imprints.

Figure 20B:
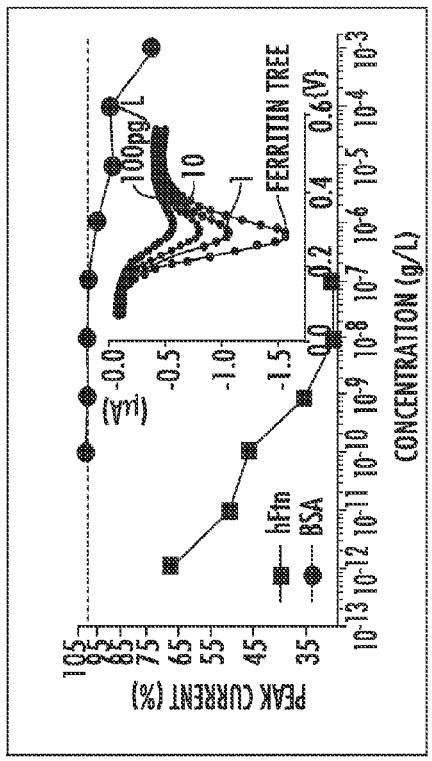
FIGS. 20-24 illustrate exemplary results of highly sensitive and selective MIP nanosensor based protein detection techniques.

The hFtn detection was conducted with EIS as well as differential pulse voltammetry (DPV). As shown in FIG. 20A, Nyquist plots demonstrate the impedance spectroscopy of the sensor at different stages of development and various levels of protein rebinding. The hypothetical impedance changes mentioned above were well demonstrated. Compared to bare sensor arrays (no PPn), the PPn coating (PPn+hFtn) increased the sensor impedance modulus from 13±2 kΩ to 241±47 kΩ (data obtained from 7 samples, f=10 Hz). The impedance vs. protein concentrations demonstrates apparent different responses for different targets. Each hFtn measurement was preceded by the measurement of a control protein, bovine serum albumin (BSA), to emphasize the contrast of the responses to ferritin and BSA. Application of hFtn in concentrations ranging from $10^{-12}$ to $10^{-7}$ g/L exhibited an increase in impedance, whereas BSA exhibited significantly smaller changes in impedance, even at $10^{-3}$ g/L. The impedance modulus at 10 Hz showed that the response to hFtn started between $10^{-12}$ and $10^{-11}$ g/L, while that of BSA was between $10^{-4}$ and $10^{-3}$ g/L. Therefore, a $10^6$ higher concentration of BSA was required to generate a similar impedance signal. The impedance approached its maximum value with $10^{-7}$ g/L of hFtn. Thus, the dynamic range of hFtn detection spans 4 decades. To verify the detection of ferritin, DPV was used to detect the faradic current corresponding to the insulation leakage by the imprints. FIG. 20B shows dose responses of faradic current vs. protein concentrations, on log-log scales. The inset is the original DPV current responding to different hFtn concentrations. The blockage of DPV current by hFtn rebinding exhibited similar dose response as that observed with EIS. Control experiments were conducted using other proteins such as horse apoferritin (aFtn) and horse ferritin (hsFtn) with concentrations up to $10^{-4}$ g/L. These control molecules did not exhibit significant effects via either EIS or DPV. Note that ferritin is a very conservative protein in mammalians, with hFtn and hsFtn having more than 92% homogeneity. Thus, discrimination of the two ferritins suggests a high selectivity of the sensor. The binary protein mixtures containing hFtn and other interfering protein molecules such as aFtn, hsFtn and a whole protein extracts from another animal were also evaluated.

Figure 20C:
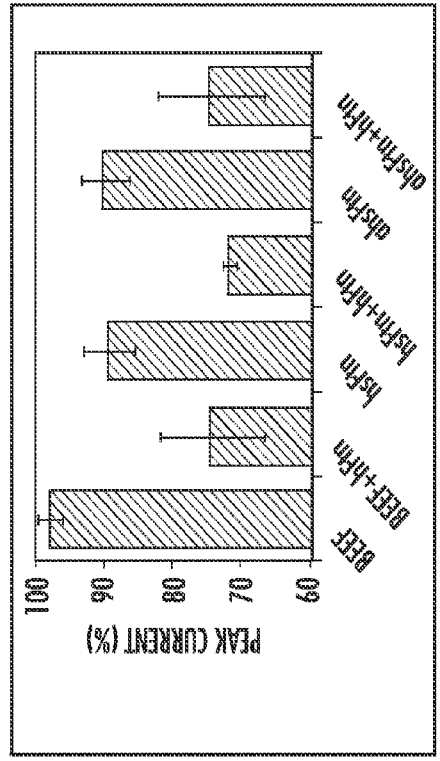
Figure 20A:
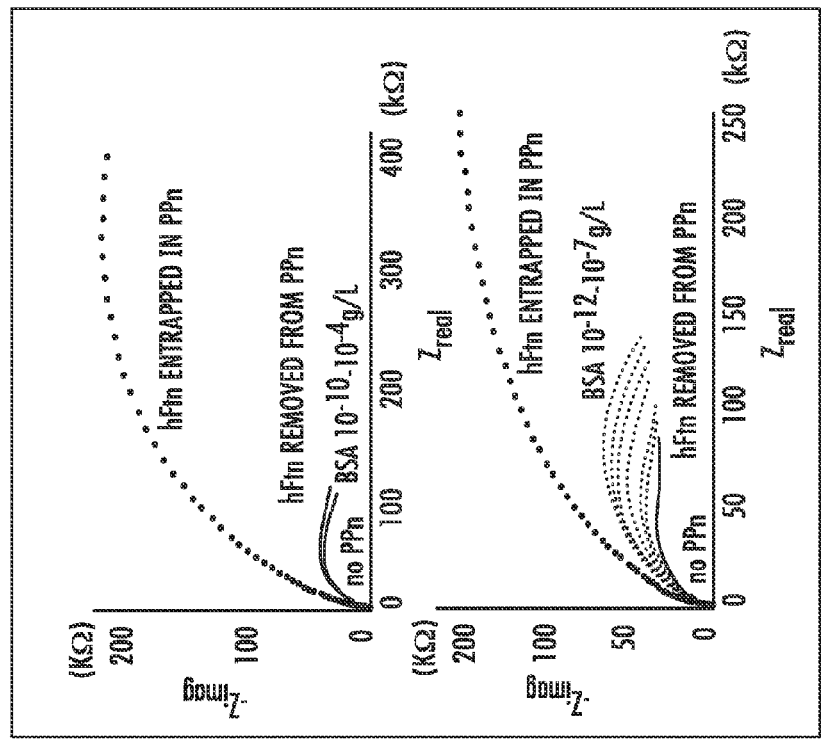

As shown in FIG. 20C, all binary mixtures exhibited DPV inhibition above the non-specific current reduction by the interfering proteins; the hFtn concentration was 1/100 of the interfering proteins. The sensor selectivity to hFtn in binary mixtures shown by DPV. All interferent proteins were prepared at 1 μg/L with each binary protein mixture prepared by mixing hFtn with the interferent protein at the final concentrations of 0.01 and 1 μg/L, respectively).

Figure 21A:
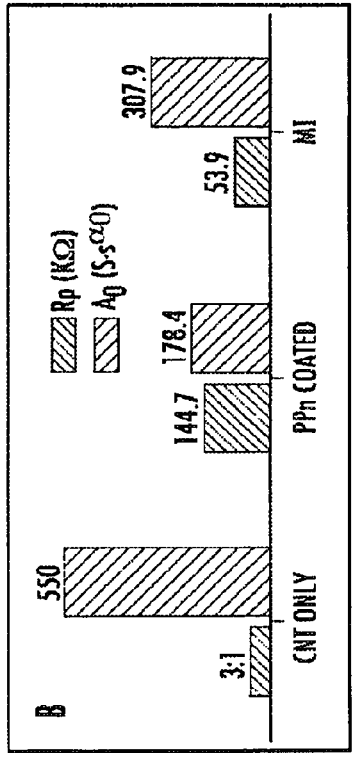

To elucidate the mechanisms of the detection, Nyquist plots were fitted with a model containing constant phase elements (CPE), as shown in FIG. 21A. $R_p$ is generally considered the PPn coating resistance. $R_u$ is the solution resistance. When $α_0$ in $CPE_0$ is close to 1, $A_0$ represents the double layer capacitance $C_{dl}$. For PPn-coated electrodes, $A_0$ is considered the capacitance of serial $C_{dl}$ and $C_{PPn}$. Accordingly, the observed impedance changes in "PPn coated" and "MI" sensors can be attributed to the alterations of resistance and capacitance. FIG. 21B shows $R_p$ and $A_0$ at various fabrication stages, such as "CNT only", "PPn coated" and "MI" (molecularly imprinted) derived from Nyquist plots fittings. Their values are displayed in log scales.)

Figure 21C:
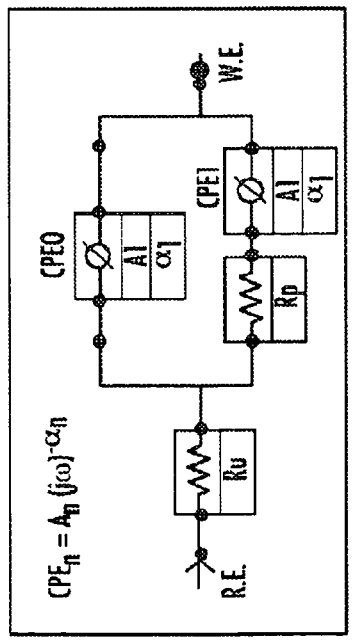
Figure 21B:
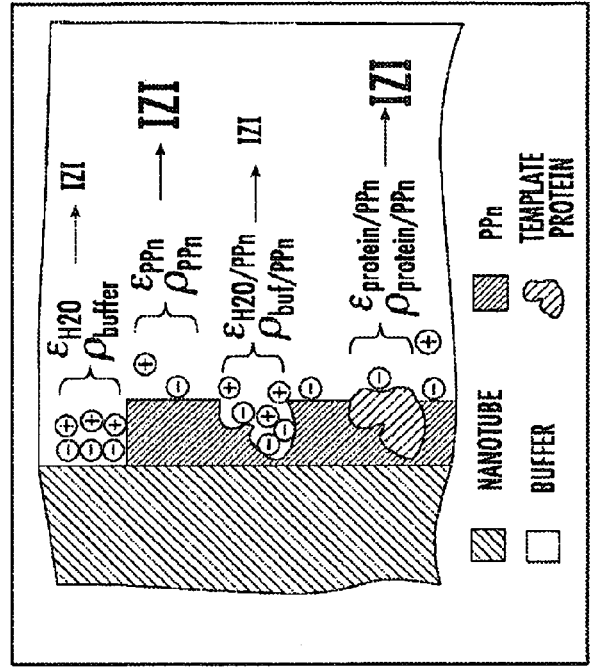

Accordingly, the previous dose-response in EIS can be described as the increase of resistance and decrease of capacitance vs. the increase of hFtn concentrations (see FIG. 21C, showing $R_p$ and $A_0$ vs. administrated ferritin and BSA concentrations). At the highest hFtn concentration, we observed a 50% resistance increase and a 20% capacitance decrease. In contrast, the non-specific binding of BSA showed an obscure fashion of resistance and capacitance changes.

Figure 21D:
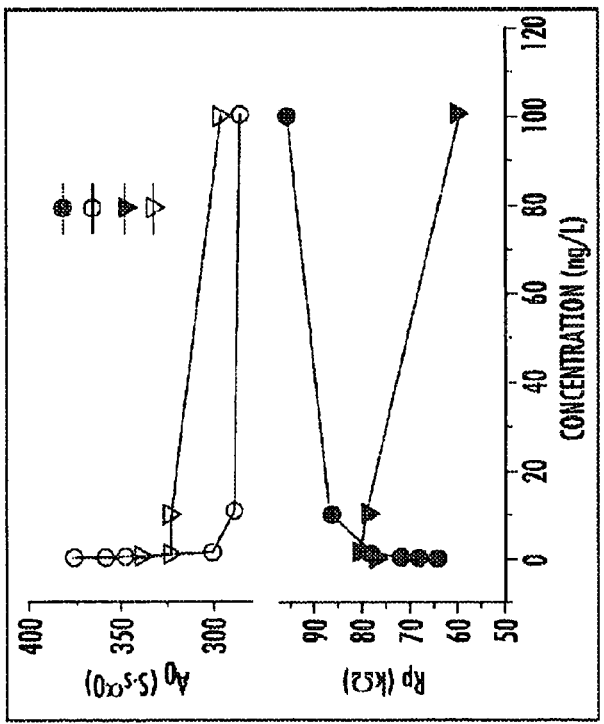
Figure 21E:
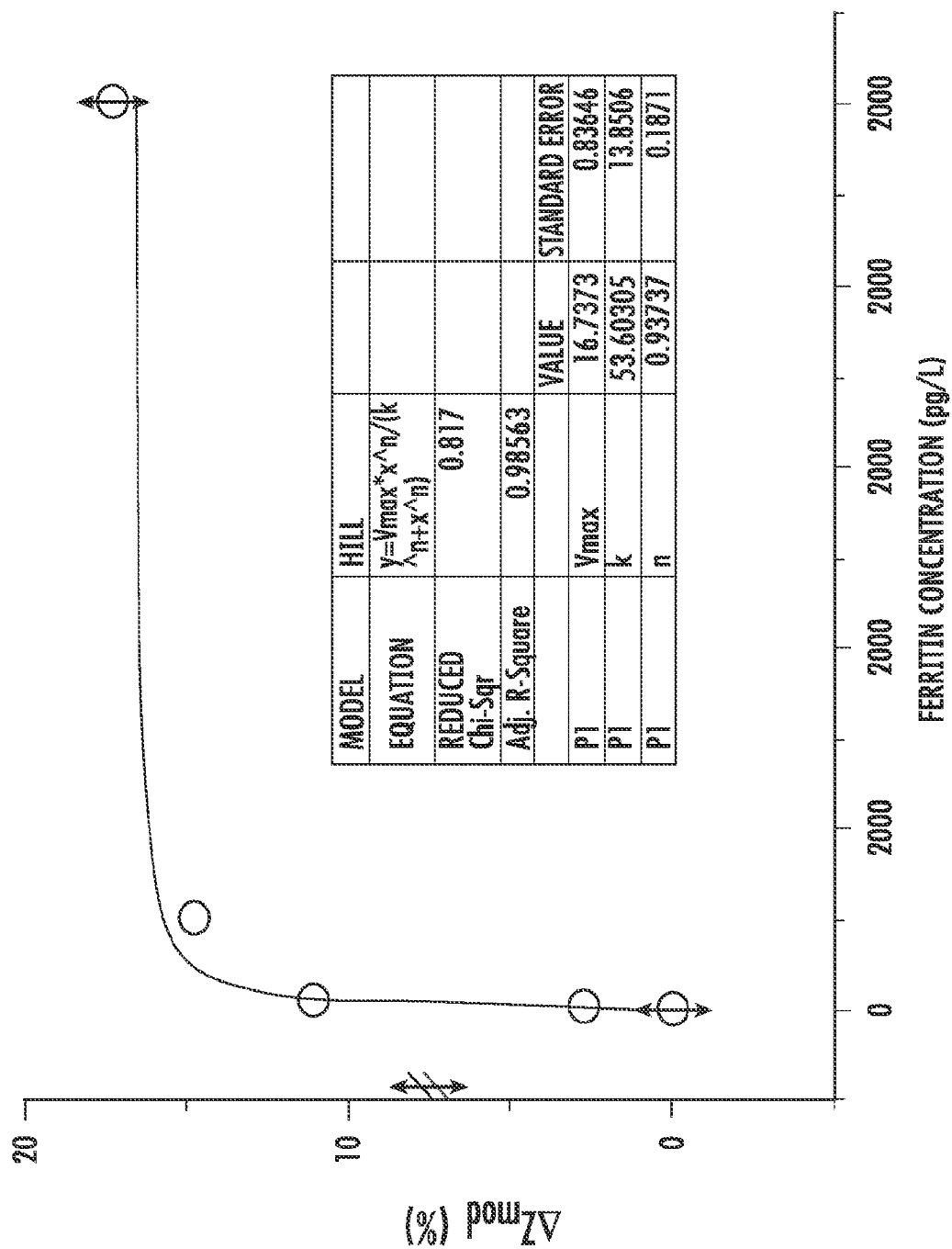

The ferritin detection data shown in FIG. 21C can be presented, as shown in FIG. 21E, as the percentage change of impedance modulus ($ΔZ_{mod}$) as a function of ferritin concentration. As shown in the inset, the data is fitted to a cooperative model, resulting in a dissociation constant of the imprint to ferritin at 53.6 pg/L. In other words, the data indicates that the above described technique is sufficiently sensitive that ferritin can be reliably detected at concentrations of 53.6 pg/L or less.

FIG. 21D illustrates possible scenarios of the sensors surfaces. Four scenarios of sensor surface conditions closely related to resistivity (ρ) and permittivity (ε): ((1) bare nanotube surface, where solution double-layer dominates the surface, ($\epsilon_{H2O}$, $\rho_{buffer}$); (2) nanotube surface coated by PPn, ($\epsilon_{PPn}$, $\rho_{PPn}$); (3) nanotube coated by PPn with imprint vials, ($\epsilon_{H2O/PPn}$, $\rho_{buffer/PPn}$); and (4) imprint with re-bound template protein, ($\epsilon_{protein/PPn}$, $\rho_{protein/PPn}$)). The change of permittivity (ε) and resistivity (ρ) in the surface materials are considered as the primary mechanism of the signaling. In brief, re-binging proteins have lower ε and higher ρ than the displaced water in the imprint space, leading to increased resistance and decreased capacitance.

Figure 22A:
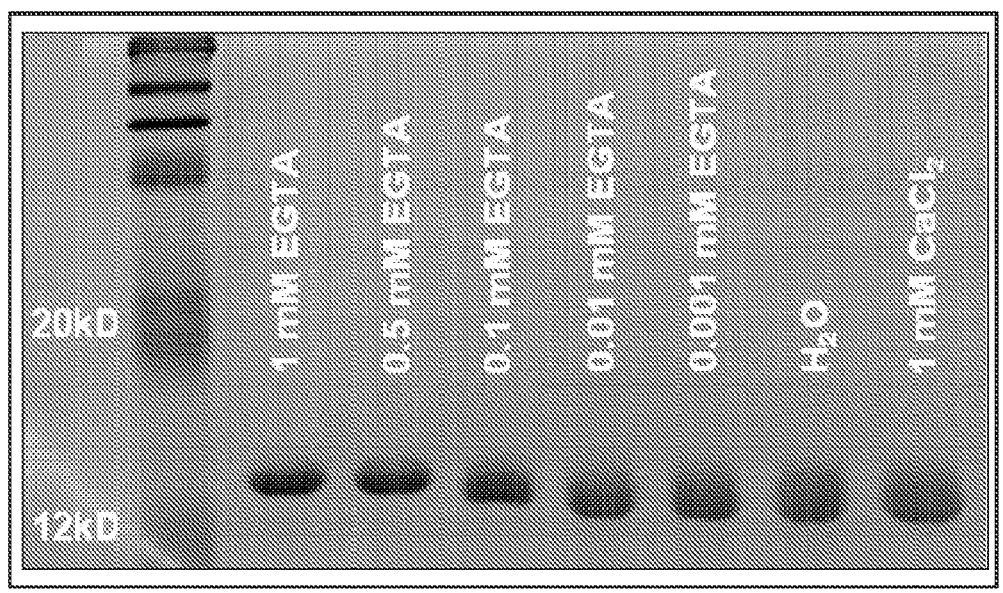

We also sought to determine if molecular imprinting could discriminate protein conformations. The protein calmodulin (CaM) was employed, due to its $Ca^{+2}$ dependent conformations. The conformational change was biochemically demonstrated by gel-shift experiments. FIG. 22A shows SDS denatured gel test of $Ca^{2+}$ induced CaM conformation change. $Ca^{2+}$ (1 mM) was balanced with EGTA at various concentrations. The gradual band shift indicates the native $Ca^{2+}$ dependency of CaM conformation.

During the co-deposition phase with PPn, 1 mM $Ca^{2+}$ was used to saturate CaM and render a full scale elongation ("open") that offered distinctive imprint morphology from its globular shape at $Ca^{2+}$ free or other partial "close" status. $Ca^{2+}$ bound CaM (Ca-CaM) was detected by DPV under various free $Ca^{2+}$ concentration buffered with ethylene glycol tetraacetic acid (EGTA). As shown in FIG. 22C, this result was confirmed using circular dichroism measurement, in which the degree of conformation change in CaM as a function of $Ca^{2+}$ concentration is a buffer solution are detected using a circular dichroism (CD) technique. As is well known in the art, CD is the differential absorption of left- and right-handed circularly polarized light be a substance. A CD spectrometer may be used to record this phenomenon as a function of wavelength and chemical environment. FIG. 22C shows the CaM CD fractional angular displacement measured as a function of wavelength for various concentrations of $Ca^{2+}$ in an EGTA buffer. The measured angular displacement corresponds to the $Ca^{2+}$ being induced CaM conformation change. Given the molecular weight of CaM is 16.8 Kd, the CaM concentration in the measurement was 5.34 μM that, at certain points, allowed all Ca-binding sites being saturated by the $Ca^{2+}$ in the buffer. The fractional angular displacements at 208 nm are fitted in the inset with the equation including cooperative information.

Figure 22B:
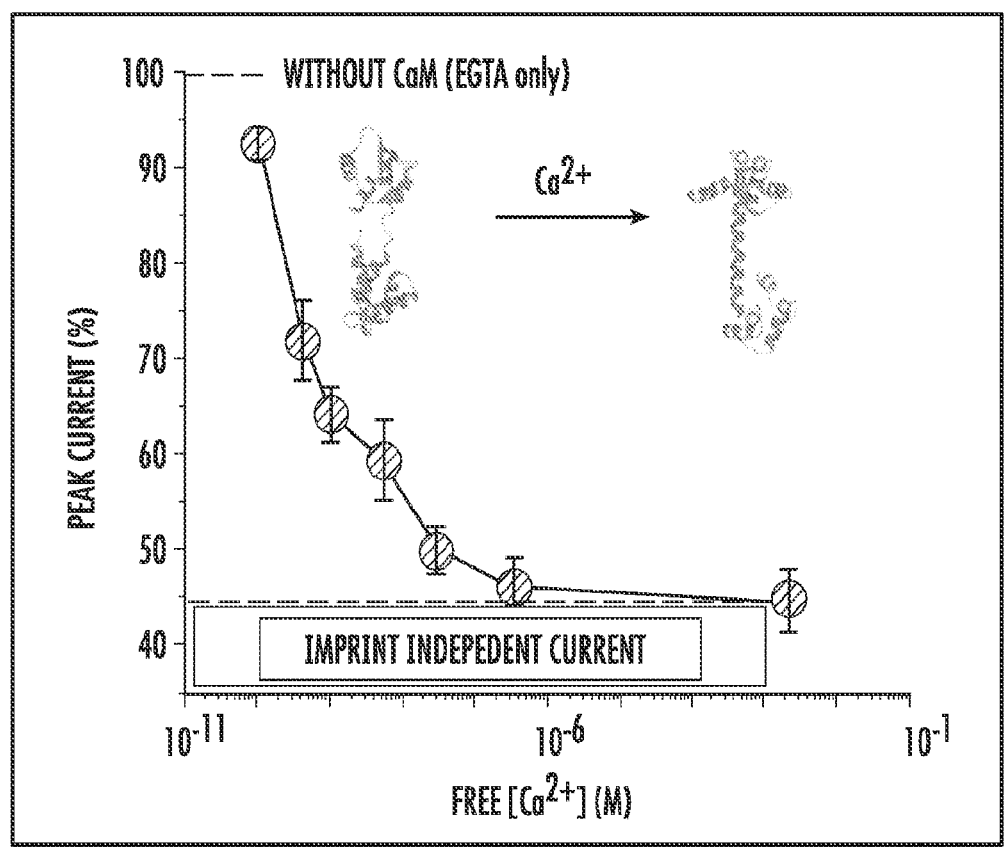
Figure 22C:
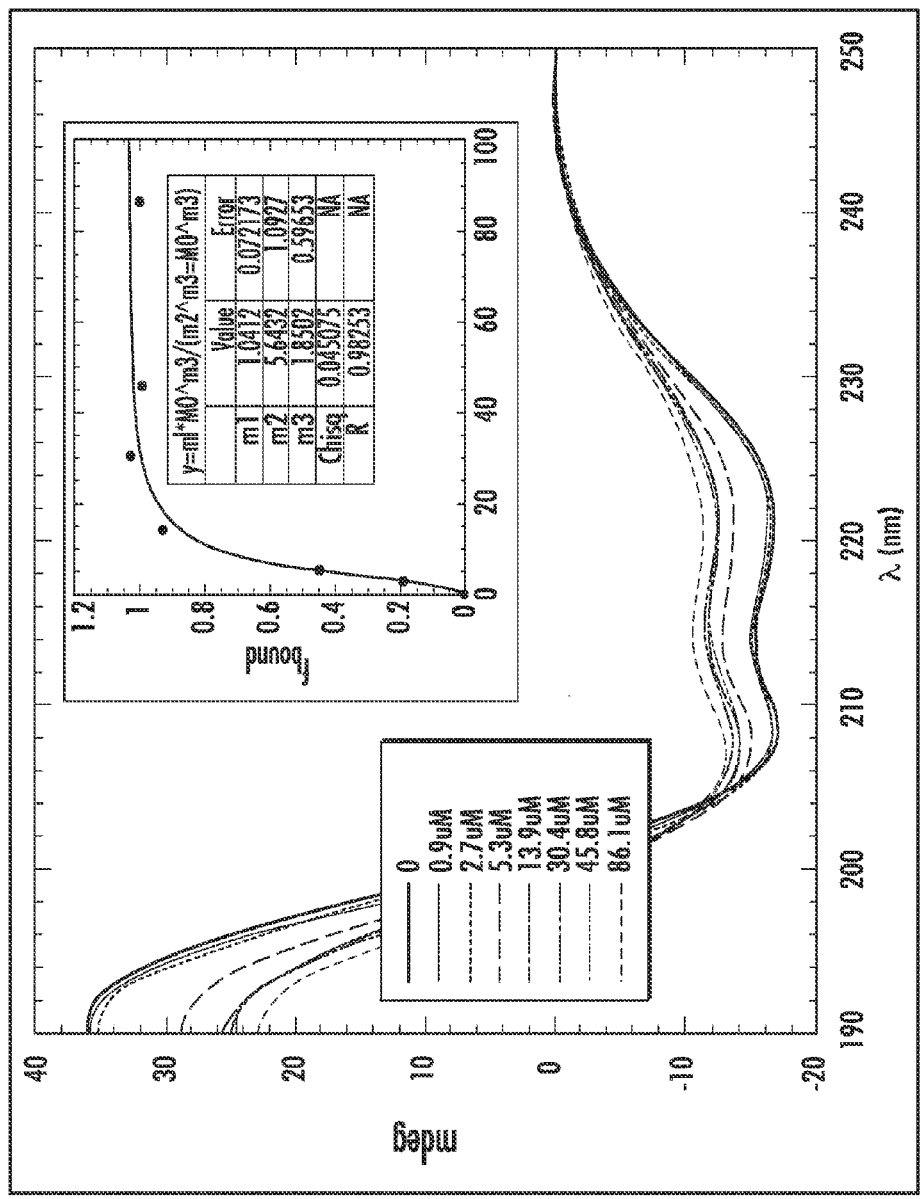

FIG. 22B shows sensor DPV peak currents inhibited by Ca-CaM. (Peak currents were normalized to that recorded in Tris buffer with 1 mM EGTA. In all other recordings, 10 mg/L CaM was added to the Tris-EGTA buffer. Addition of different amounts of $CaCl_2$ yielded the designated free $[Ca^{2+}]$. Imprint-independent current represents the total residual current that was not sensitive to even overloaded $Ca^{2+}$. $K_d^{EGTA}=$ 207 nM. n=4. Error bars stand for S.E.M.). DPV current was inhibited at 0.2 nM free $Ca^{2+}$ and exhibited a half maximum inhibition at approximately 1 nM, reflecting a high sensitivity and selectivity to Ca-CaM.

In summary, the sensor reported herein offers the advantage of highly sensitive, label-free detection of proteins, with a detection limit of ~10 pg/L hFtn, equivalent to 20 aM, a $10^4$ times improvement over previous imprint-based "peptide" sensors, and 100 times greater sensitivity than antibody-based nanosensors. The present molecular imprint-based detection scheme also offers flexibility for the detection of a range of molecules, from organic compounds to macromolecules. Moreover, it may prove useful for detecting conformational changes in proteins that might be incurred as a result of post-translational modification, mutation or ligand binding. Finally, the sensor holds promise for the detection of macromolecules in situations where conventional means of detection (e.g. antibody-based recognition) are not feasible.

In the above example, periodic CNT arrays were first prepared as described above. The arrays were then modified by spin coating a SU8 photopolymer film followed by mechanically polishing to expose the tips of the CNTs. A PPn film was deposited on the exposed tips by cyclic voltammetry in PBS containing 1.5 mM phenol (pH=7.4). The array was then connected as a working electrode. Potential was scanned 5 times from 0 to 0.9 V versus a reference electrode at 50 mV/s. In order to entrap ferritin in the PPn nanocoating, the protein was added to the PPn deposition buffer at 100 μg/ml. Following electrophoretic attraction by applying 300 mV DC voltage for 30 s, cyclic voltammetric voltages were used to form PPn as previously mentioned, with the co-deposition of ferritin. For EIS measurements, a 10 mV peak-to-peak sine wave was superimposed on a 300 mV DC voltage. DPV was conducted with initial and final potentials settings of 0 and 0.5 V, respectively. Other parameters defined by the manufacturer were set as: pulse size 50 mV, pulse time 0.05 s; step size 2 mV, and sample period 0.1 s. Imprint development was based on previous described procedures.

Example

Detection of HPV Biomarker

Cervical cancer is worldwide the second most common cancer in women. It is estimated that annually there are over 470,000 new cases and 233,000 deaths. Detecting cancers in the pre-malignant state is critically important, as early detection would allow for appropriate treatment modalities to be initiated prior to the onset of metastasis, thereby reducing mortality and morbidity, potentially significantly so.

Research has revealed that nearly all cervical cancers (99.7%) are directly linked to previous infection with one or more of the oncogenic types of HPV. There are total about 100 kinds of HPV with some of them malignancy related and termed as "high risk" virus. Therefore, unlike other cancers, the early detection of cervical cancer has two concerns: (1) identifying if there is high-risk virus; and (2) examining if there are oncogenisis signals that indicate malignancy of the tissue. Biomarkers are biological substances (such as, nucleic acid, lipids, or proteins) that can be used to detect disease (particularly for cancers), measure its progression, or monitor the efficacy of therapeutic intervention. The diagnostic biomarkers detection techniques in use today are not only insufficient of early detection, but may also suffer from a lack of sensitivity or specificity.

In the HPV genome, a significant role for malignant transformation can be assigned to the early gene E6 and E7 genes and their respective proteins. Both E6 and E7 proteins can bind to multiple cellular targets. Initial observations revealed that E6 interacts with p53, and E7 interacts with pRb to block the activity of these tumour suppressors. Indeed, some of the prominent functions of the E6 protein originate from its interaction with, followed by degradation of p53, and the pro-apoptotic protein Bak, which results in resistance to apoptosis and an increase in chromosomal instability. E7, however, interacts with pRb-associated pocket proteins, which are negative cell cycle regulators involved in the G1/S and G2/M transitions. The interaction between E7 and pRb results in enhanced phosphorylation and degradation of pRb. pRb destruction leads to the release of the transcription factor E2F, upregulates p16 (i.e. INK4A) and subsequent activation of genes promoting cell proliferation. Since E6, E7, p53, pRb, and p16 proteins are closely related to HPV induced pathogenesis, they are considered as biomarkers of cervical cancer.

Figure 23:
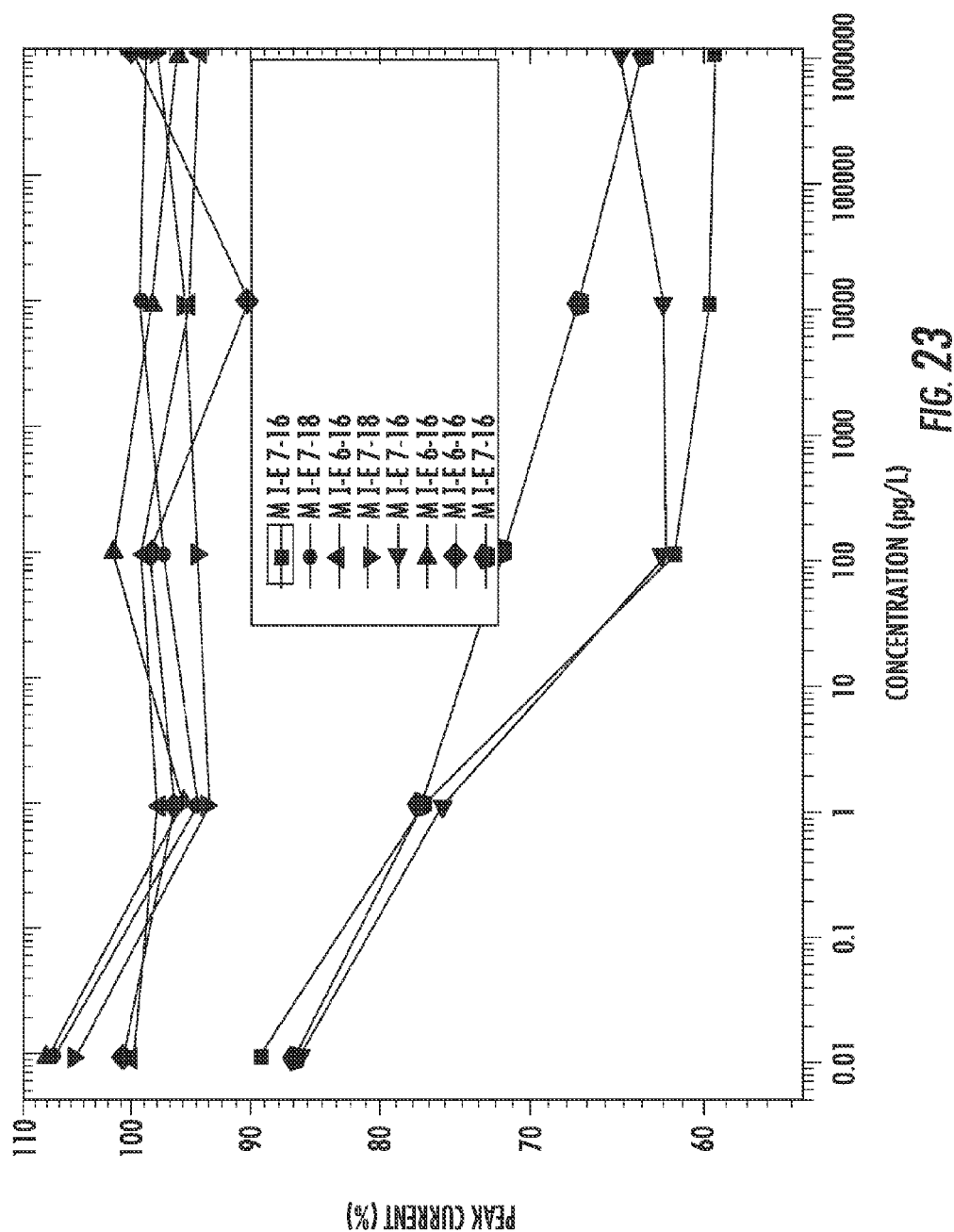

MIP nanosensors of the type described herein can be provide highly sensitive and selective detection of biomarkers, e.g. those associated with pathogenic HPV. For example, referring to FIG. 23, MIP nanosensor was imprinted with the E7 type 16 protein. The peak current response of the sensor is plotted against sample concentration for a variety of E6 and E7 proteins. As shown, the sensor exhibits significant response to E6 type 16 at concentrations as low as about 0.1 pg/L. Further, the sensor is highly selective for E6 type 16, as demonstrated by the clearly distinguishable response to E7 type 18 and E6 type 16 proteins.

It is to be understood that although the specific example of detecting HPV biomarkers have been discussed in detail, the above describe techniques can be applied for use in detecting other biomarkers, e.g. those associated with the H1N1 influenza virus.

Example

Streptavidin Imprint

Figure 24:
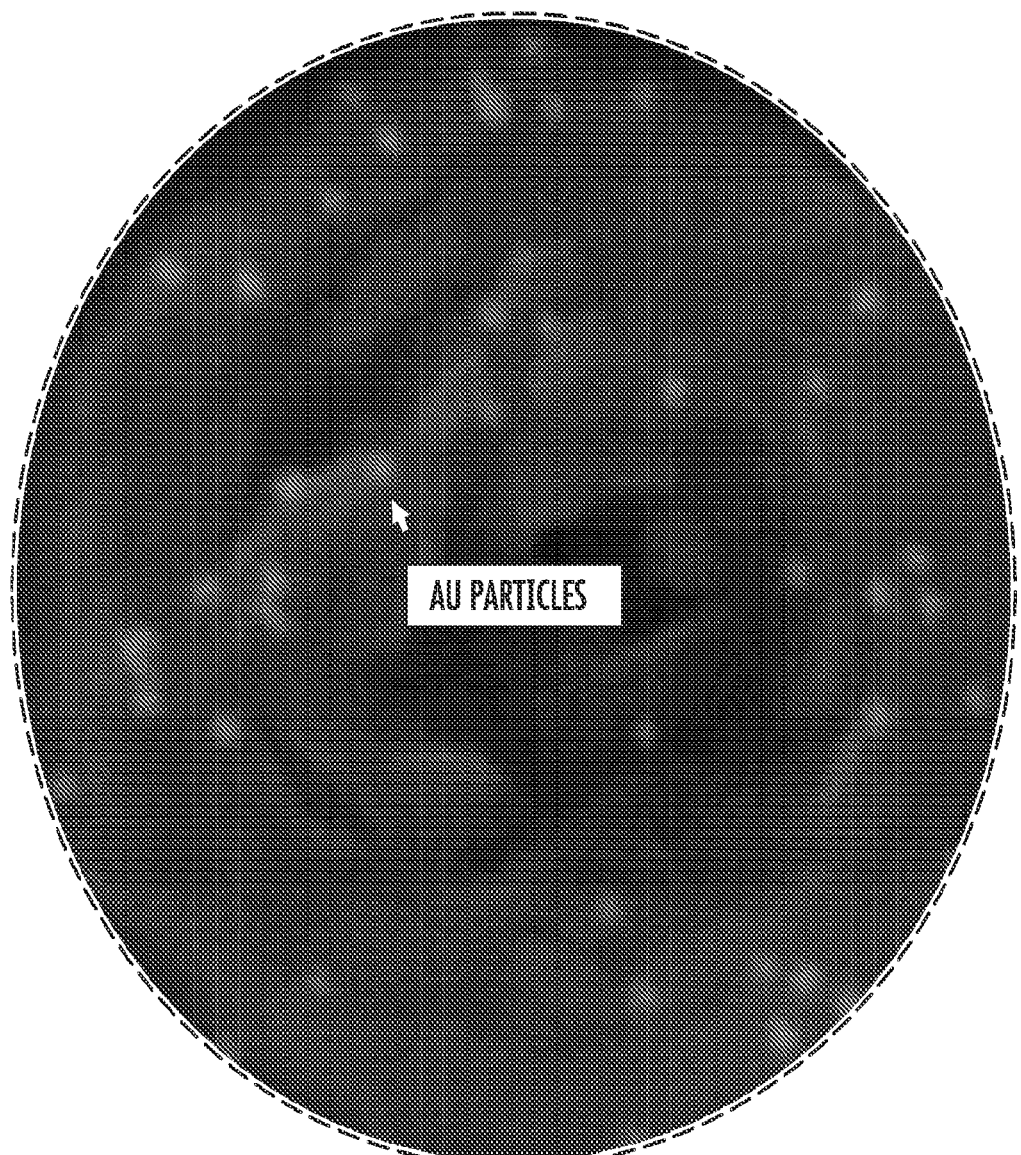

Referring to FIG. 24, we used streptavidin to imprint the PPn coated tips of a tCNTA sensor using the techniques described herein. After the rebinding of streptavidin was electrochemically observed as with protein detection as described above. The sample was incubated at room temperature with PBS buffer supplemented with biotinylated gold particles for 20 min. Following rinse, the sample was fixed with 3.7% formaldehyde. As shown in FIG. 24, tips (one shown, indicated with a dashed circle) of the tCNTA were imaged with an SEM. The biotinylated gold particles associated with (i.e. bonded to) the streptavidin molecules bound to the imprinted PPn coating are visible as bright dots on the SEM image. Thus, the number of gold particles mentioned above is an indirect indication of the streptavidin. On average, there were 40 gold particles per nanotubes. A control sample was coated with unimprinted PPn only but experienced the same process as the imprint sample. No particle was observed on the CNT tips of the control.

Additional Embodiments

A number of embodiments are described herein. Nevertheless, it will be understood that various modifications may be made without departing from the spirit and scope of the invention.

For example, although several of the embodiments described herein feature conductive CNTs, other nanostructures can be used including conductive, non-conductive, or semi-conductive nanostructures. The nanostructures may include nanowires, nanorods, nanoparticles, or a combination thereof. The nanostructures may be arranged in any suitable configuration, including vertically, horizontally, randomly, etc.

Although several embodiments described herein feature PPn MIP films, other suitable films may be used. For example, phenolic oxide polymers can be used for the same sensor development by electropolymerizing phenol, p-cresol, 4-chlorophenol, 2,4-dichlorophenol, pyrogallol, 3-nitrophenol, 4-hydroxybenzene-sulfonoc acid, bromophenol blue, etc. Other suitable non-conductive polymers include poly (indole), poly(o-phenylene-diamine), poly(7,14-diphenylacenaphtho[1,2-k]fluoranthene), etc. Some embodiments may include imprinting conductive or semi-conductive polymer nanocoating on nanostructures. The typical conductive polymers include poly(pyrrole), poly(n-methylpyrrole) and poly(aniline).

Although several embodiments described herein feature impedance measurements to determine the presence of a target molecule, any measurement scheme may be used. For example, any physical, chemical, electrochemical, optical, electrical or any other suitable property of the nanostructure and/or MIP film may be used.

Examples of suitable electrochemical detection methods include: chronoamperometry, chronocoulometry, chronopotentiometry, cyclic voltammetry, linear sweep voltammetry, differential pulse voltammetry, square wave voltammetry, normal pulse voltammetry, reverse normal pulse voltammetry, differential pulse stripping voltammetry, square wave stripping voltammetry, normal pulse stripping voltammetry, reverse normal pulse stripping voltammetry, galvanostatic EIS (electrochemistry impedance spectroscopy), hybrid EIS, potentiostatic EIS, single frequency EIS.

In some embodiments, the target molecules may include a fluorescent tag, and detection may include detection of light from target molecules trapped by the MIP.

In some embodiments, the imprint techniques described herein may by applied to target structures other than molecules.

Other aspects, features, and advantages are within the scope of the invention.

What is claimed is:

1. An apparatus for detecting the presence of a target molecule comprising:
    a conductive nanostructure;
    a non-conductive polymer coating on at least a portion of the nanostructure, the non-conductive polymer coating defining a cavity having a shape corresponding to the shape of the target molecule wherein the thickness of at least a portion of the non-conductive polymer coating is less than or about equal to the size of the cavity; and
    a detection unit configured to produce a signal indicative of the presence of the target molecule at the cavity based on a measured change in a property of the nanostructure, wherein the property of the nanostructure depends on the binding of the target molecule with the non-conductive polymer coating at the cavity, and wherein the polymer coating is self-limiting under electro polymerization and comprises a polyphenol film.

2. The apparatus of claim 1, wherein the thickness of the non-conductive polymer coating is less than about 15 nm.

3. The apparatus of claim 1, wherein the property of the nanostructure comprises the impedance of the nanostructure.

4. The apparatus of claim 1, wherein the nanostructure comprises an array of substantially aligned carbon nanotubes each extending from a surface to a respective distal tip.

5. The apparatus of claim 4, further comprising a protective layer surrounding the array such that only the distal tip of each nanotube extends from the layer; and wherein the non-conductive polymer coating comprises a film on the distal tip of each nanotube.

6. The apparatus of claim 1, wherein the impedance modulus of the nanostructure is reduced in the presence of the target molecule at the cavity.

7. The apparatus of claim 1, comprising a plurality of cavities formed in the polymer coating each having a shape corresponding to the shape of the target molecule and wherein the impedance of the nanostructure depends on the occupation of the cavities by target molecules.

8. The apparatus of claim 7, wherein the detection unit is configured to produce a signal indicative of the concentration of target molecules present in an environment proximal to the nanostructure, the signal being based on the impedance of the nanostructure.

9. The apparatus of claim 8, wherein the detection unit is configured to produce a signal indicative of the concentration of target molecules with a sensitivity of about 10 picograms per liter or less.

10. The apparatus of claim 9, wherein the detection unit is configured to produce a signal indicative of the concentration of target molecules with a sensitivity of about 1 picogram per liter or less.

11. The apparatus of claim 10, wherein the target molecule comprises ferritin.

12. The apparatus of claim 1, wherein the nanostructure comprises at least one from the list consisting of: a nanoparticle, a nanorod, a nanowire, a nanotube.

13. The apparatus of claim 1, wherein the property comprises at least one selected from the list of: a mechanical property, a chemical property, and electrochemical property, an optical property, and an electrical property.

14. The apparatus of claim 1, wherein the target molecule comprises at least one selected from the list comprising: a protein molecule, a pheromone molecule, an explosive molecule.

15. An apparatus for detecting the presence of a target molecule comprising:
 a conductive nanostructure comprising a carbon nanotube;
 a non-conductive polymer coating comprising a polyphenol film on at least a portion of the nanostructure, the non-conductive polymer coating defining a cavity having a shape corresponding to the shape of the target molecule, wherein the thickness of at least a portion of the non-conductive polymer coating is less than or about equal to the size of the cavity, and wherein the impedance of the nanostructure depends on the binding of the target molecule with the non-conductive polymer coating at the cavity; and
 a detection unit configured to produce a signal indicative of the presence of the target molecule at the cavity based on a measured change in the impedance of the nanostructure.

16. The apparatus of claim 15, wherein the nanostructure comprises an array of substantially aligned carbon nanotubes each extending from a surface to a respective distal tip.

17. The apparatus of claim 16, further comprising a protective layer surrounding the array such that only the distal tip of each nanotube extends from the layer; and wherein the non-conductive polymer coating comprises a film on the distal tip of each nanotube.

18. The apparatus of claim 15, wherein the impedance modulus of the nanostructure is reduced in the presence of the target molecule at the cavity.

19. The apparatus of claim 15, comprising a plurality of cavities formed in the polymer coating each having a shape corresponding to the shape of the target molecule and wherein the impedance of the nanostructure depends on the occupation of the cavities by target molecules.

20. The apparatus of claim 19, wherein the detection unit is configured to produce a signal indicative of the concentration of target molecules present in an environment proximal to the nanostructure, the signal being based on the impedance of the nanostructure.

21. The apparatus of claim 20, wherein the detection unit is configured to produce a signal indicative of the concentration of target molecules with a sensitivity of about 10 picograms per liter or less.

22. The apparatus of claim 21, wherein the detection unit is configured to produce a signal indicative of the concentration of target molecules with a sensitivity of about 1 picogram per liter or less.

23. The apparatus of claim 22, wherein the target molecule comprises ferritin.

24. The apparatus of claim 15, wherein the nanostructure further comprises at least one from the list consisting of: a nanoparticle, a nanorod, a nanowire.

25. The apparatus of claim 15, wherein the target molecule comprises at least one selected from the list comprising: a protein molecule, a pheromone molecule, an explosive molecule.

26. The apparatus of claim 15, wherein the thickness of the non-conductive polymer coating is less than about 15 nm.

27. The apparatus of claim 15, wherein the polymer coating is self-limiting under electro polymerization.

* * * * *